United States Patent
Bonney et al.

(10) Patent No.: US 7,500,444 B2
(45) Date of Patent: Mar. 10, 2009

(54) ACTUATION INDICATOR FOR A DISPENSING DEVICE

(75) Inventors: Stanley George Bonney, Ware (GB); Peter John Brand, Ware (GB); James William Godfrey, Ware (GB); Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 565 days.

(21) Appl. No.: 10/518,421

(22) PCT Filed: Jun. 19, 2003

(86) PCT No.: PCT/EP03/06466

§ 371 (c)(1),
(2), (4) Date: Dec. 17, 2004

(87) PCT Pub. No.: WO04/001664

PCT Pub. Date: Dec. 31, 2003

(65) Prior Publication Data

US 2006/0096594 A1  May 11, 2006

(30) Foreign Application Priority Data

Jun. 21, 2002 (GB) ................................. 0214360.0
May 15, 2003 (GB) ................................. 0311191.1

(51) Int. Cl.
*G06M 1/24* (2006.01)
*G09F 11/04* (2006.01)

(52) U.S. Cl. .................. 116/311; 116/317; 128/205.23

(58) Field of Classification Search .................. 116/284, 116/285, 307, 309, 311–318; 128/200.23, 128/205.23; 221/6, 7, 8; 222/36, 38; 235/1 C, 235/91 R
See application file for complete search history.

(56) References Cited

U.S. PATENT DOCUMENTS

| | | | | |
|---|---|---|---|---|
| 3,718,114 | A * | 2/1973 | Gneupel | 116/299 |
| 4,817,822 | A * | 4/1989 | Rand et al. | 222/38 |
| 6,067,927 | A * | 5/2000 | Johnson et al. | 116/227 |
| 6,360,739 | B1 | 3/2002 | Rand et al. | |
| 6,431,168 | B1 | 8/2002 | Rand et al. | |
| 6,474,331 | B1 | 11/2002 | Rand et al. | |
| 6,601,582 | B2 | 8/2003 | Rand et al. | |
| 7,107,986 | B2 | 9/2006 | Rand et al. | |

(Continued)

FOREIGN PATENT DOCUMENTS

JP   06152159 A * 5/1994

(Continued)

OTHER PUBLICATIONS

Patent Abstracts of Japan 006(195):146 (Oct. 1982) JP57 103585, Jun. 28, 1982, abstract.

*Primary Examiner*—R. A. Smith
(74) *Attorney, Agent, or Firm*—J. Michael Strickland

(57) ABSTRACT

An actuation indicator that includes a drum sub-assembly, which includes a rotatable actuation indicator wheel, a rocking, ratchet pawl for rotating the indicator wheel in a set direction and a rocking mechanism for the pawl driven by a slipping clutch arrangement, is described. The slipping clutch arrangement includes a slipping clutch spring engaged at one end to a pinion of a rack and pinion assembly and at a second end to the ratchet pawl.

6 Claims, 20 Drawing Sheets

U.S. PATENT DOCUMENTS

2002/0047021 A1  4/2002  Blacker et al.
2006/0289008 A1  12/2006  Rand et al.

FOREIGN PATENT DOCUMENTS

| WO | 9856445 A1 | 12/1998 |
| WO | 9856446 A1 | 12/1998 |
| WO | WO 98/56444 | 12/1998 |
| WO | WO 01/28887 | 4/2001 |

* cited by examiner

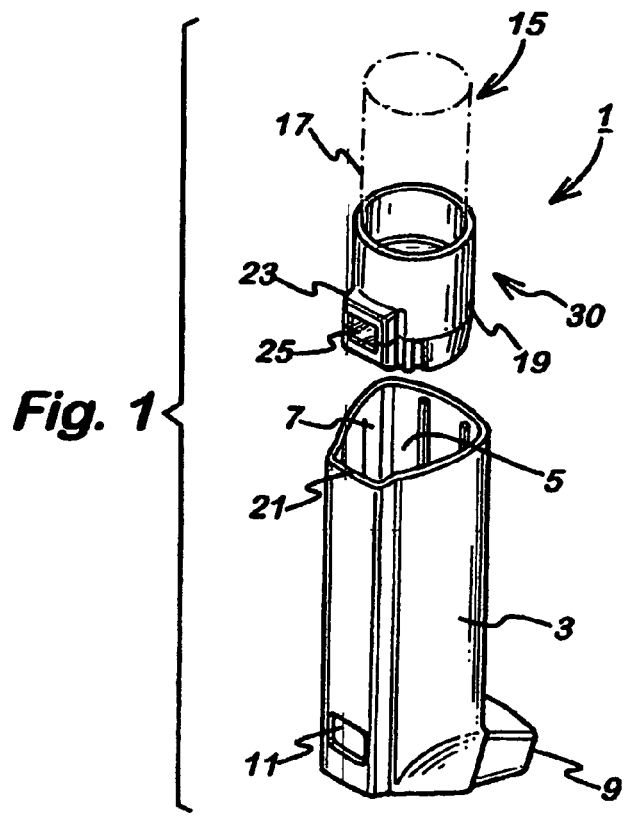
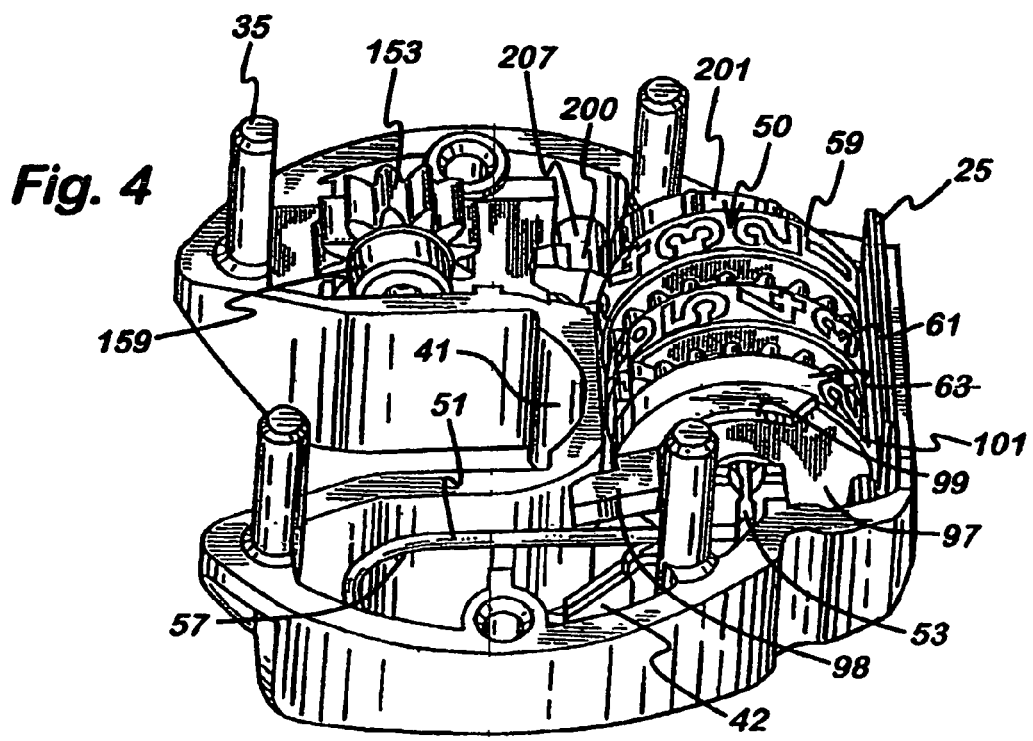

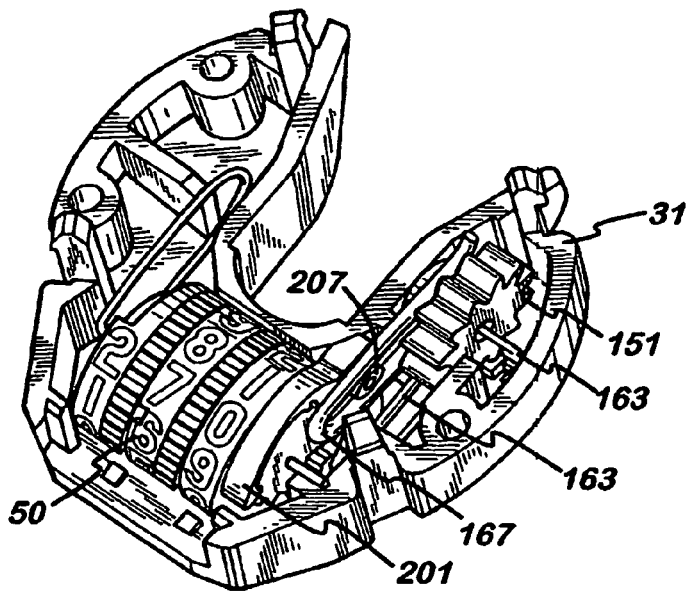
Fig. 6
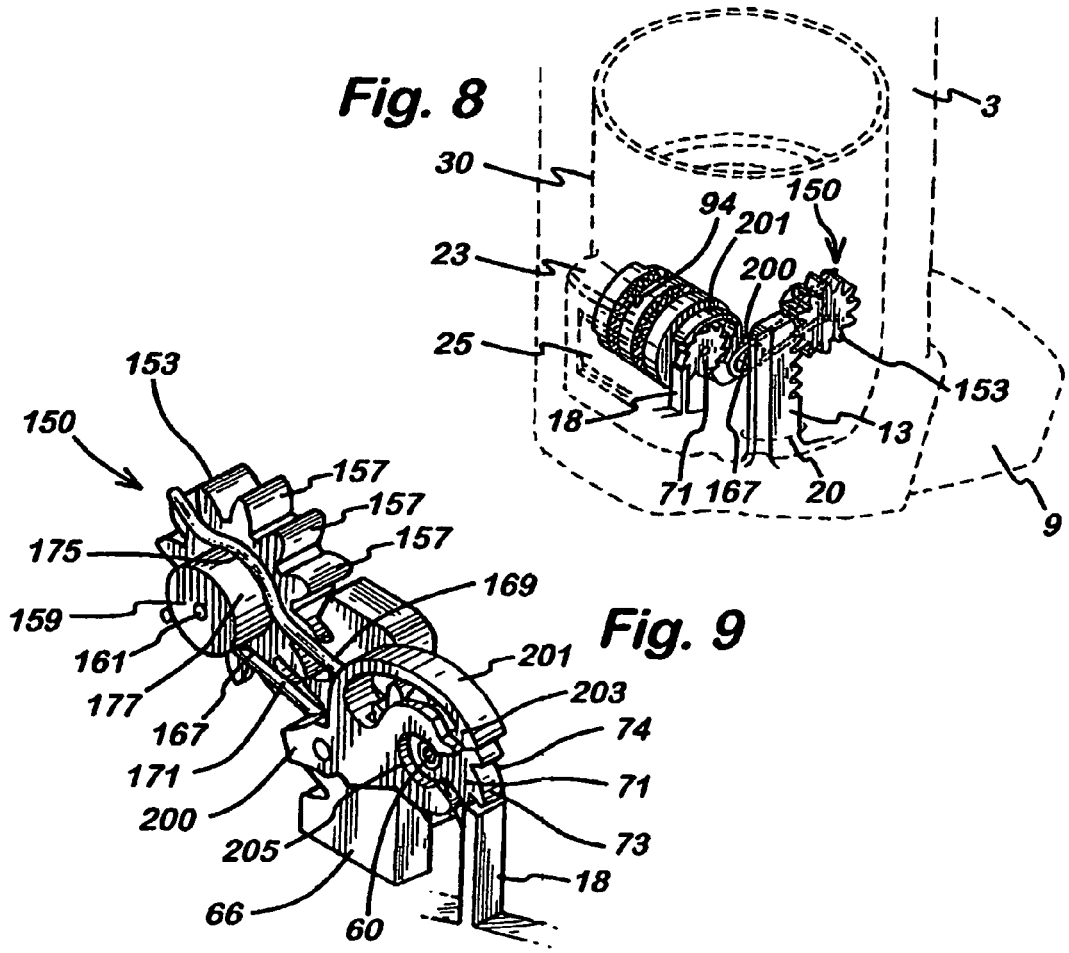
Fig. 8
Fig. 9

Mechanism at rest

Mechanism at rest

Start of downstroke

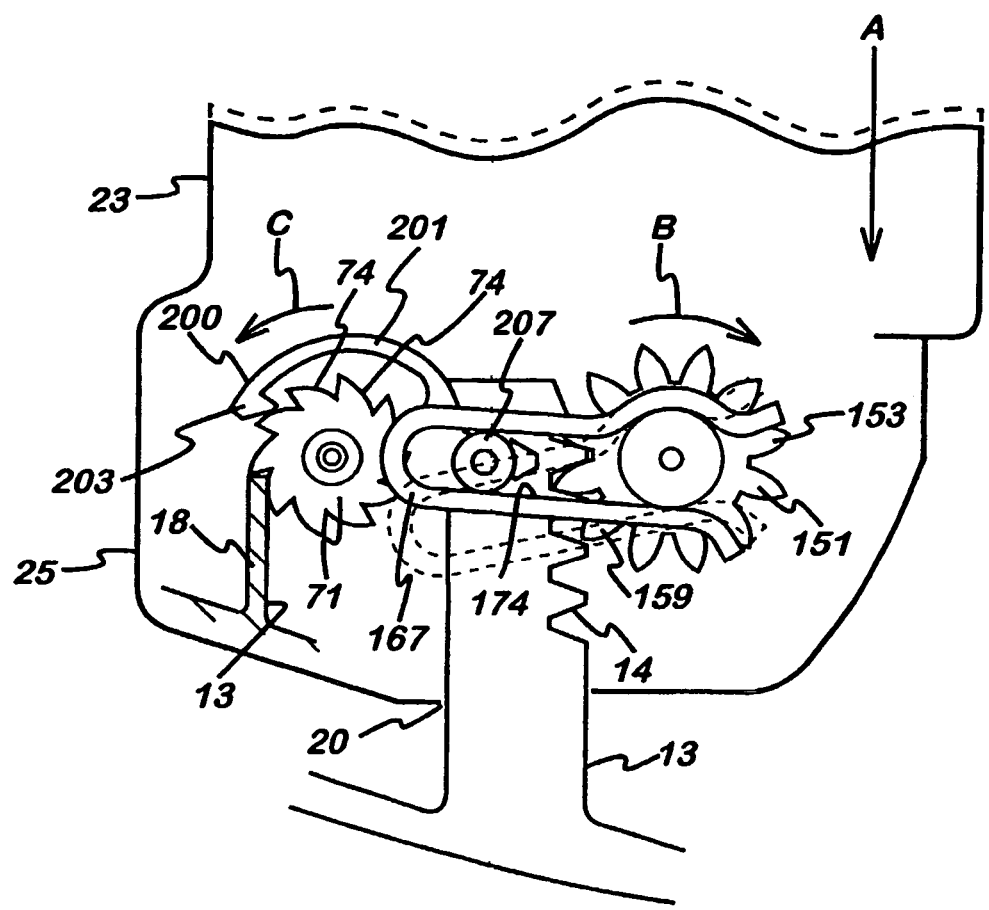

Bottom of downstroke

Bottom of downstroke

Return stroke

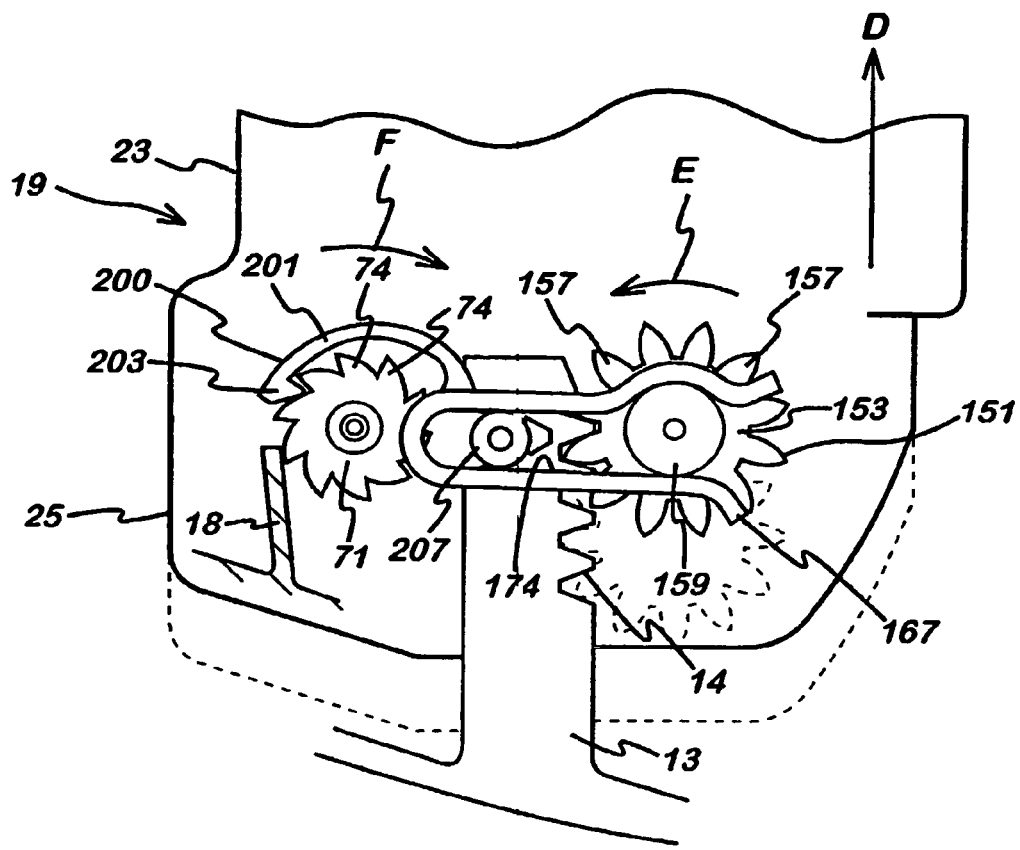

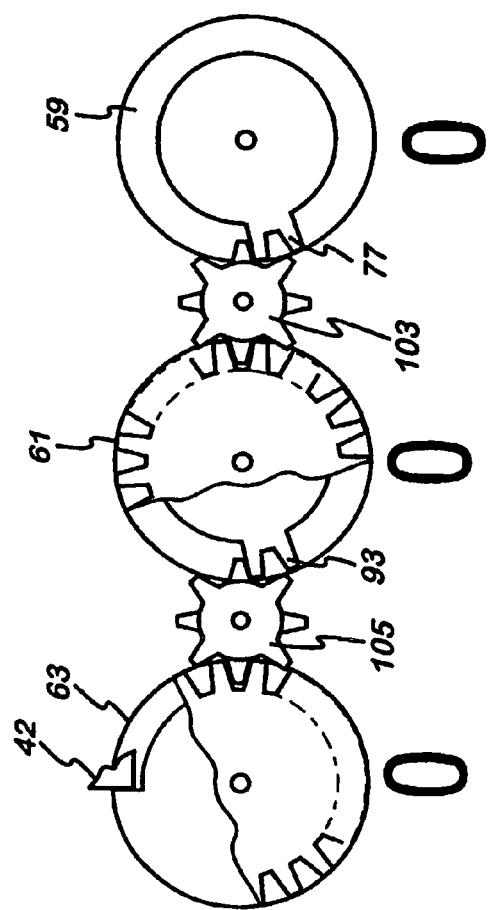
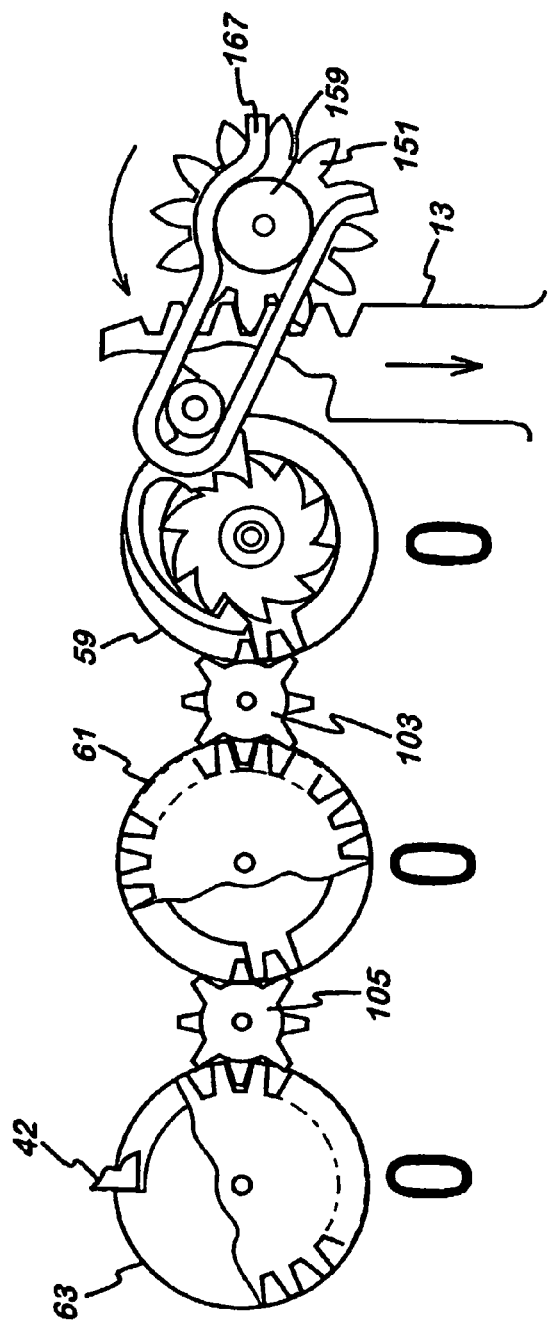
Fig. 17A
Fig. 17B

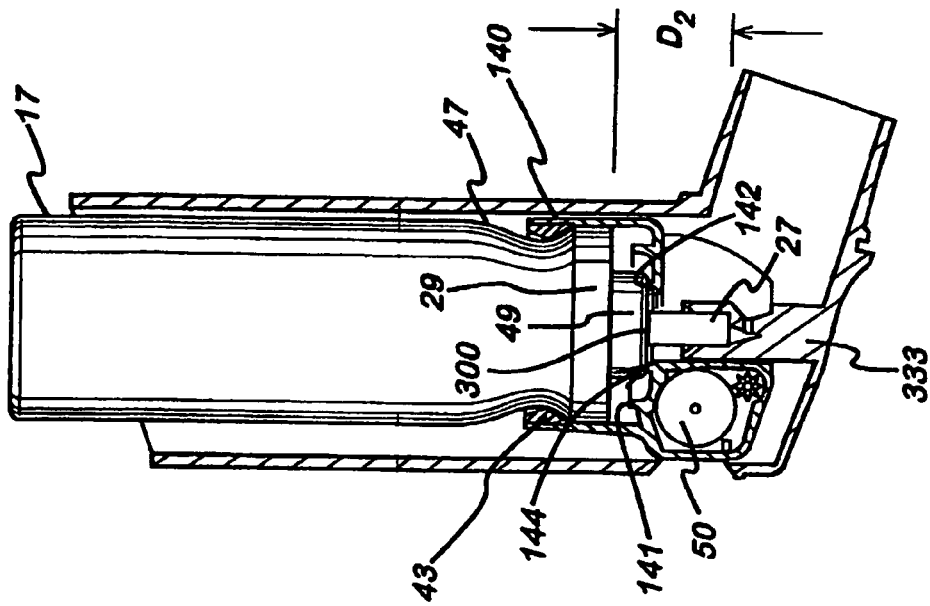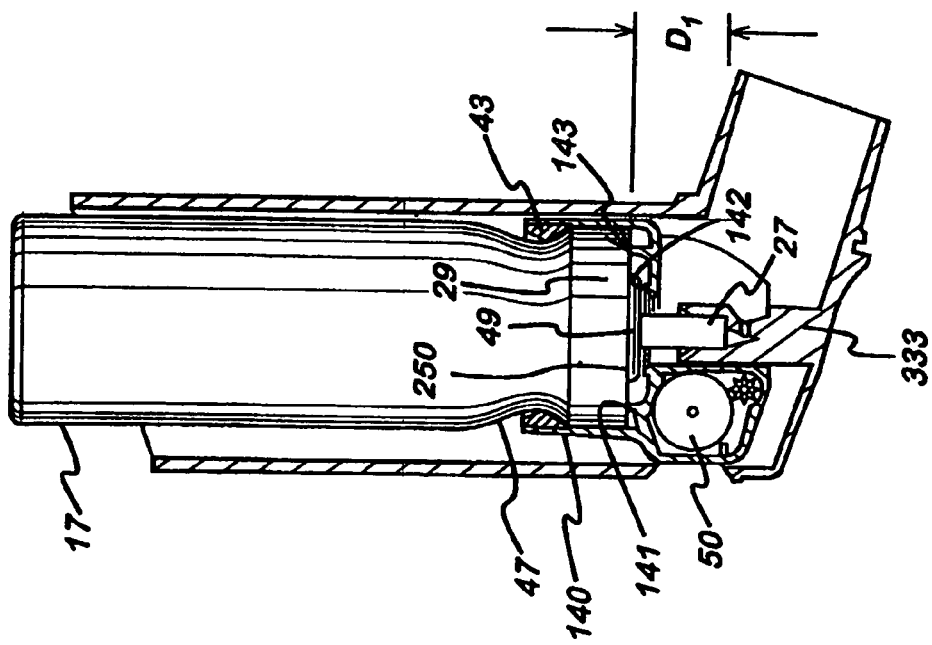

ACTUATION INDICATOR FOR A DISPENSING DEVICE

This application is filed pursuant to 35 U.S.C. § 371 as a United States National Phase Application of International Patent Application Serial No. PCT/EP2003/006466 filed Jun. 19, 2003, which claims priority from Great Britain Application No. 0214360.0 filed in the United Kingdom on Jun. 21, 2002 and Great Britain Application No. 0311191.1 filed May 15, 2003.

RELATED APPLICATION

The present application claims priority from UK patent application No. 0214360.0 filed 21 Jun. 2002 and UK patent application No. 0311191.1 filed 15 May 2003, the entire contents of which are hereby incorporated herein by reference.

FIELD OF THE INVENTION

The present invention relates to an actuation indicator for a dispensing device, e.g. a fluid dispensing device or pressurised fluid dispensing device, such as a pressurised metered dose inhaler (hereinafter referred to as a "pMDI"), and components of such an actuation indicator.

BACKGROUND OF THE INVENTION

"pMDIs" are well known in the art of inhalation devices. It is therefore not necessary to describe the construction and operation of a PMDI other than in bare essentials.

A PMDI comprises an aerosol canister and a tubular actuator.

The aerosol canister comprises a pressurised can, typically made from a metal, such as aluminium. Inside the can there is contained the pressurised medicinal aerosol formulation. The can is sealingly capped by a metering valve assembly at what will hereinafter be referred to as the "outlet end" of the aerosol canister. The valve assembly includes a hollow dispensing member or valve stem which projects from the outlet end of the aerosol canister. The dispensing member is mounted for sliding movement relative to the aerosol canister between an extended position, to which the dispensing member is biased by a biasing mechanism in the valve assembly, and a depressed position.

Movement of the dispensing member from the extended position to the depressed position results in a metered dose of the aerosol formulation being dispensed from the canister through the dispensing member.

The tubular actuator comprises an internal passageway having an open end. The aerosol canister is slidable into the internal passageway through the open end with the outlet end being inserted first into the internal passageway.

The actuator has a stand or stem block which receives the dispensing member of the aerosol canister when the aerosol canister is received in the actuator in a "rest position". The stand has a passageway with an inlet end for receiving the dispensing member and an outlet end which faces a mouthpiece of the actuator. The stand holds the dispensing member stationary in the actuator whereby depression of the aerosol canister from its rest position farther into the actuator to an "actuated position" causes the dispensing member to be displaced from the extended position to the depressed position relative to the canister. A metered dose of the aerosol formulation will thereby be dispensed out of the mouthpiece of the actuator via the internal passageway of the stand.

In use, a patient in need of a metered dose of the medicinal aerosol formulation places their lips on the mouthpiece of the actuator and then concurrently inhales and depresses the aerosol canister from the rest position to the actuated position. The inspiratory airflow produced by the patient entrains the medicinal, component of the aerosol into the patient's respiratory tract.

Instead of a mouthpiece, there could be provided a nozzle for nasal use.

Developments to these pMDIs have included the provision of actuation indicators therefor, for instance dose counters which are either incremented on each actuation of the pMDI to display a running total of the number of doses dispensed from the pMDI or decremented on each actuation to display the number of doses left in the dispenser. See, for example, W096/16686, U.S. Pat. Nos. 4,817,822 and 5,482,030.

A recently developed dose counter is described in PCT Patent Application No. W098/56444, to Glaxo Group Limited, the entire contents of which are incorporated herein by way of reference. The dose counter is fixably secured on the outlet end of the aerosol canister and includes a display which denotes the number of metered doses of the medicament formulation left in the aerosol canister. The display of the dose counter is visible to the patient through a window provided in the actuator. The display is presented by a plurality of indicator wheels rotatably mounted on a common axle, each wheel having numerals from '0' to '9' displayed in series around the circumference.

Before the dose counter is mounted on the aerosol canister, the display wheels are arranged so that the display shows the claimed total number of doses available in the aerosol canister, the so-called "label claim". Upon each actuation, an indexing mechanism in the dose counter comprising a star wheel, a driver yoke and a rack operates to decrement the number displayed by the display by rotation of one or more of the indicator wheels.

When the aerosol canister with attached dose counter is in a rest position in the actuator, the rack, which is formed in the actuator, protrudes into the dose counter. When the aerosol canister is moved from the rest position to the actuated position, this results in relative movement between the dose counter and the rack. During this relative movement, the rack engages the yoke of the indexing mechanism to cause it to operate to decrement the number displayed by the display by turning the star wheel. The index mechanism of the mechanical dose counter known from W098/56444 includes a lost motion coupling to compensate for overtravel of the dose counter relative to the rack as the aerosol canister reciprocates between the rest position and the actuated position in the actuator.

A device and method for attaching a dose counter to an aerosol canister is disclosed in PCT application publication WO01/28887, also to Glaxo Group Limited, the entire contents of which are incorporated herein by way of reference. The dose counter is fixedly secured to the outlet end of the aerosol canister through a split-ring collar. More particularly, a skirt portion of the dose counter housing surrounds a neck on the can of the aerosol canister, and the split-ring collar is wedged in-between the skirt and a re-entrant surface of the neck and then ultrasonically welded to the skirt. This effectively provides a permanent connection between the dose counter and the aerosol canister to prevent the dose counter from being tampered with.

All these prior art devices, however, require the components thereof to be manufactured to tight tolerances so that they correctly function, or they are difficult to assemble. Accordingly, they are relatively expensive to manufacture.

Further, they are unsuitable for attachment to canisters or actuators that are made with wide manufacturing tolerances, as may occur when attempting to reduce the manufacturing cost of actuators or aerosol canisters.

It would be desirable to provide an actuator and/or dose counter that is inexpensive to manufacture due to the lack of the need for tight manufacturing tolerances. It would also be desirable to provide an actuator and/or dose counter that is simple and therefore inexpensive to assemble. It would also be desirable to provide an actuator and/or dose counter that can be used with more than one size of aerosol canister. It would also be desirable to provide components of such devices that allow for wide manufacturing tolerances.

SUMMARY OF THE INVENTION

According to a first aspect of the present invention there is provided an axle of a rotatable element of an actuation indicator (e.g. a dose counter), wherein the axle is provided by a spring that is adapted in use to bias the rotatable element towards another element of the actuation indicator with which the rotatable element is engaged. The other element may be for causing rotation of the rotatable element, or caused to be rotated by the rotatable element. This biasing allows the two elements to be made with wide tolerances while still being able to operate correctly together.

Preferably the rotatable element is a pinion.

Preferably the other element with which the pinion engages is a rack, for instance extending through the dose counter.

Preferably the rotatable element is an indicator wheel for indicating actuation of a device with which the indicator is associated, e.g. for indicating at least a part of a count of the number of doses of a substance left in, or dispensed from, a dispensing device.

Preferably there are at least two rotatable elements on the axle, for instance three rotatable elements as in the exemplary embodiment hereinafter to be described. The rotatable elements may respectively be a units wheel and a tens wheel, and hundreds wheel where there is a third rotatable element, for indicating a dose count.

Preferably the other element is a rotatable element mounted on a second, preferably parallel, axle. More preferably, the second axle is also provided by the spring.

The present invention further provides an axle assembly comprising the axle, the rotatable element(s) on the spring axle and the other element.

Preferably the spring also comprises a biasing section which connects the axles and biases the axles towards one another. The section may (i) be U-shaped, (ii) have substantially parallel sides and (iii) be substantially perpendicular to the two axles.

The present invention further provides an actuation indicator comprising a drums sub-assembly comprising a rotatable actuation indicator wheel, a rocking, ratchet pawl for rotating the indicator wheel in a set direction and a rocking mechanism for the pawl driven by a slipping clutch arrangement, wherein the slipping clutch arrangement comprises a slipping clutch spring engaged at one end to a pinion of a rack and pinion assembly and at a second end to the ratchet pawl.

Preferably the slipping clutch spring has a generally U-shaped configuration.

Preferably the open end of the spring engages a boss of the pinion and the closed end of the spring defines a track for slidingly engaging a boss provided on the pawl.

Preferably the ratchet pawl engages a ratchet wheel that is fixed to the indicator wheel.

Preferably a resilient, non-return leg engages a tooth of the ratchet wheel to prevent rotation of the ratchet wheel in a direction other than the set direction, and the non-return leg rides up and over the teeth to allow rotation in the set direction.

Preferably there are at least two indicator wheels arranged to sequentially count down from a set figure to zero, there being at least a tens wheel and a units wheel, wherein the indicator wheels lock from further rotation in the set direction when they have counted down to zero, the slipping clutch spring then slipping upon further attempts to rotate the mechanism.

The present invention also provides a casing adapted to be attached over a valve stem end of a canister to form a canister unit, the casing comprising a sleeve part having a generally cylindrically shaped section having a generally cylindrical inner surface extending from a top of the sleeve part towards a base wall, and a collar affixable around a neck of the canister, and sized, when around the neck of the canister, to fit through the top of the sleeve part, into the sleeve part, whereat it will contact at least a portion of the generally cylindrical inner surface, wherein the generally cylindrical inner surface has a shoulder for supporting the collar to prevent the collar from being inserted further into the sleeve part, the shoulder being spaced from the top and the base wall of the sleeve part.

In accordance with the invention in all its aspects, the canister unit may be a pressurised canister unit, such as an aerosol canister unit, e.g. for use in a pressurised metered dose inhaler.

Preferably the top of the sleeve part comprises a chamfered surface to assist with the insertion of the collar into the sleeve part.

Preferably the shoulder is formed by an annular step in the generally cylindrical inner surface.

Preferably the shoulder is formed by a ledge attached to the generally cylindrical inner surface.

Preferably the collar is a split ring collar.

Preferably the collar, in an assembled canister unit, is welded to the sleeve part.

The present invention also provides a casing adapted to be attached over a valve stem end of a canister to form a canister unit, the casing comprising a sleeve part for receiving a canister and a cap part for receiving a counter assembly of a dose counter for the canister unit, where the cap part and counter assembly can be assembled together separate from the sleeve part and canister, the sleeve part and cap part then being joinable together to form the casing.

Preferably, the casing further comprises a counter assembly, the counter assembly comprising a drums sub-assembly.

Preferably the sleeve part is adapted to receive more than one form or type of valve stem end, e.g. pressurised fluid canisters fitted with different valves.

Preferably the sleeve part comprises a top through which, in use, a valve stem end of the canister will be inserted and a base wall spaced from the top having more than one support thereon, each support being for supporting a different form of valve stem end, whereby more than one different valve stem end can be supported in the sleeve part.

Preferably the supports are annular ledges.

Preferably the ledges are concentric.

Preferably a first said support is of a first height above the base wall and a second said support is of a lesser height above the base wall.

The present invention also provides components for the above casing comprising a cap part and at least two sleeve parts, the two sleeve parts being for different valve stem ends, wherein the cap part is joinable to any one of the sleeve parts to form a casing for a chosen valve stem end.

The present invention also provides a sleeve part for receiving a valve stem end of a canister, the sleeve part being adapted to receive more than one form of valve stem end.

Preferably the sleeve part comprises a top through which, in use, a valve stem end of the canister will be inserted and a base wall spaced from the top having more than one support thereon, each support adapted for supporting a different form of valve stem end, whereby more than one different form of valve stem end is able to be supported in the sleeve part.

Preferably the supports are annular ledges.

Preferably the ledges are concentric.

Preferably a first support is of a first height above the base wall and the second support is of a lesser height above the base wall.

The present invention further provides a drug product for dispensing a drug formulation comprising a propellant and a medicament comprising:
a housing;
a container containing the drug formulation having an outlet member and adapted to be actuable within the housing; and,
an actuation indicating assembly, fixedly attached to the container, comprising:
a body cradle having a post;
a drive wheel adapted to engage the post and to frictionally engage a slipping clutch;
a ratchet pawl adapted to engage the slipping clutch;
a star wheel adapted to engage the ratchet pawl; and
one or more drums adapted to engage the star wheel;
wherein the fixedly attached container and actuation indicating assembly are reversibly removable from the housing as a single unit.

Preferably there are three drums adapted to display a count of 000 to 999. Preferably, the product further comprises an arm affixed to a hundred's drum adapted to contact a stop, wherein the slipping clutch is adapted to frictionally slip when the count reaches 000.

Preferably the drug product comprises a hundred's drum having numerals 0, 1 and 2, a ten's drum having numerals 0 through 9 and a one's drum having numerals 0 through 9.

Preferably the actuation indicating assembly includes one or more grip members adapted to fixedly engage a neck portion of the container.

Preferably the housing includes a mouthpiece.

Preferably the housing includes a passage adapted to pass doses from the container to the mouthpiece.

Preferably the container includes a metering valve adapted to dispense metered doses.

Preferably a window is provided, adapted to display numerals on one or more drums engaging the star wheel.

Preferably the actuation indicating assembly is fixed to the container by an adhesive, a welded shrink sleeve, a heat form, a crimp, an ultrasonic weld, an o-ring elastomer, or a split-ring collar.

Preferably the actuation indicating assembly is permanently fixed to the container.

Preferably the medicament is selected from the group consisting of beclomethasone, fluticasone, flunisolide, budesonide, rofleponide, mometasone, triamcinolone, noscapine, albuterol, salmeterol, ephedrine, adrenaline, fenoterol, formoterol, isoprenaline, metaproterenol, terbutaline, tiotropium, ipratropium, phenylephrine, phenylpropanolamine, pirbuterol, reproterol, rimiterol, isoetharine, tulobuterol, (−)-4-amino-3,5-dichloro-α-{{{6-{2-(2-pyridinyl) ethoxy}hexyl}methyl}benzenemethanol, esters, solvates and salts thereof, and combinations thereof.

Preferably the medicament is albuterol sulphate, salmeterol xinafoate, fluticasone propionate, beclomethasone dipropionate or the combination of salmeterol xinafoate and fluticasone propionate. The medicament may also be salmeterol xinafoate and a salt, ester or solvate of ipratropium.

Preferably the housing is constructed from polypropylene.

Preferably one or more components of the actuation indicating assembly is constructed from polypropylene. Preferably the drug product further comprises one or more knock gears adapted to engage the one or more drums.

Preferably the drug product comprises first, second and third drums and first and second knock gears.

The present invention also provides a method of patient compliance comprising the acts of:
providing a drug product as described above,
administering the drug formulation to a patient,
counting down a number of available doses remaining in the container on the actuation indicating assembly, and,
indicating the number of available doses remaining in the container to the patient.

Preferably the container is over-filled with up to 40 actuations.

Preferably the actuation indicating assembly locks out when the count reaches 000, and wherein the drug product remains actuable for up to 40 subsequent actuations.

The present invention further provides a drug product for dispensing a drug formulation comprising a propellant and a medicament comprising:
a housing;
a container containing the drug formulation having an outlet member and adapted to be actuable within the housing; and,
an actuation indicating assembly, fixedly attached to the container, comprising:
a body cradle having a post;
a means for driving a slipping clutch means adapted to engage the post and to frictionally engage the slipping clutch means for grasping a ratcheting means;
a pawl means for ratcheting a star wheel adapted to engage the slipping clutch means;
a star wheel adapted to engage the pawl ratcheting means; and
one or more drums adapted to engage the star wheel;
wherein the fixedly attached container and actuation indicating assembly are reversibly removable from the housing as a single unit.

Preferably the drug product comprises first, second and third drums. Preferably the drug product further comprises a means for stopping the first drum.

Preferably the drug product further comprises a first means for knock locking the first and second drums and a second means for knock locking the second and third drums.

Preferably the drug product is further adapted to indicate a count of 000 to 999 and further adapted to lock the drums when the count indicates 000.

The present invention further provides a dispensing device, e.g. for dispensing a fluid, on which is mounted an actuation indicator either according to the invention or having one or more of the different aspects of the invention as a component thereof. The actuation indicator will be adapted to be operated upon each actuation of the dispensing device to indicate said actuation of the device. Preferably, the actuation indicator will be in the form of a dose counter which displays a numerical count of the number of doses of the content of the device left to be dispensed, or the number of doses dispensed. On actuation of the device, the numerical count is either incremented or decremented, depending on whether the count is of doses left or of doses dispensed. Preferably, the dispensing device has a dispensing or outlet end and the actuation indicator is mounted on this end. Preferably, the dispensing device is an aerosol canister having a can and a valve assembly at the outlet end. The valve assembly may be a metering valve assembly, as for example where for use in a pressurised metered dose inhaler.

These and other aspects of the present invention will now be described by way of example with reference to the accompanying drawings.

BRIEF DESCRIPTION OF THE DRAWINGS

FIG. 1 is a schematic perspective view of a pressurised metered dose inhaler (pMDI) having a dose counter module mounted on the outlet end of an aerosol canister unit containing a pressurised medicinal aerosol formulation.

FIG. 4 is a first perspective view of a cap part of the dose counter module with the drums sub-assembly and drive wheel sub-assembly mounted therein.

FIG. 6 is a yet further perspective view of the cap part.

FIG. 8 is a schematic perspective view of the dose counter module inside an actuator of the pMDI, showing the drums and drive wheel sub-assemblies and a rack formed inside the actuator through which the drive wheel sub-assembly is driven.

FIG. 9 is a schematic rear perspective view of the drive wheel sub-assembly showing a toggle link-type lost motion coupling through which drive from the drive wheel sub-assembly is transmitted to the drums sub-assembly.

FIGS. 17A-B are schematic views illustrating the lockout operation.

FIGS. 22 and 23 are sections through a pMDI having a canister unit inserted in an actuator, the canister in FIG. 22 having a valve of a first configuration and the canister in FIG. 23 having a valve of a second, different configuration.

DETAILED DESCRIPTION OF THE DRAWINGS

Figure 2:
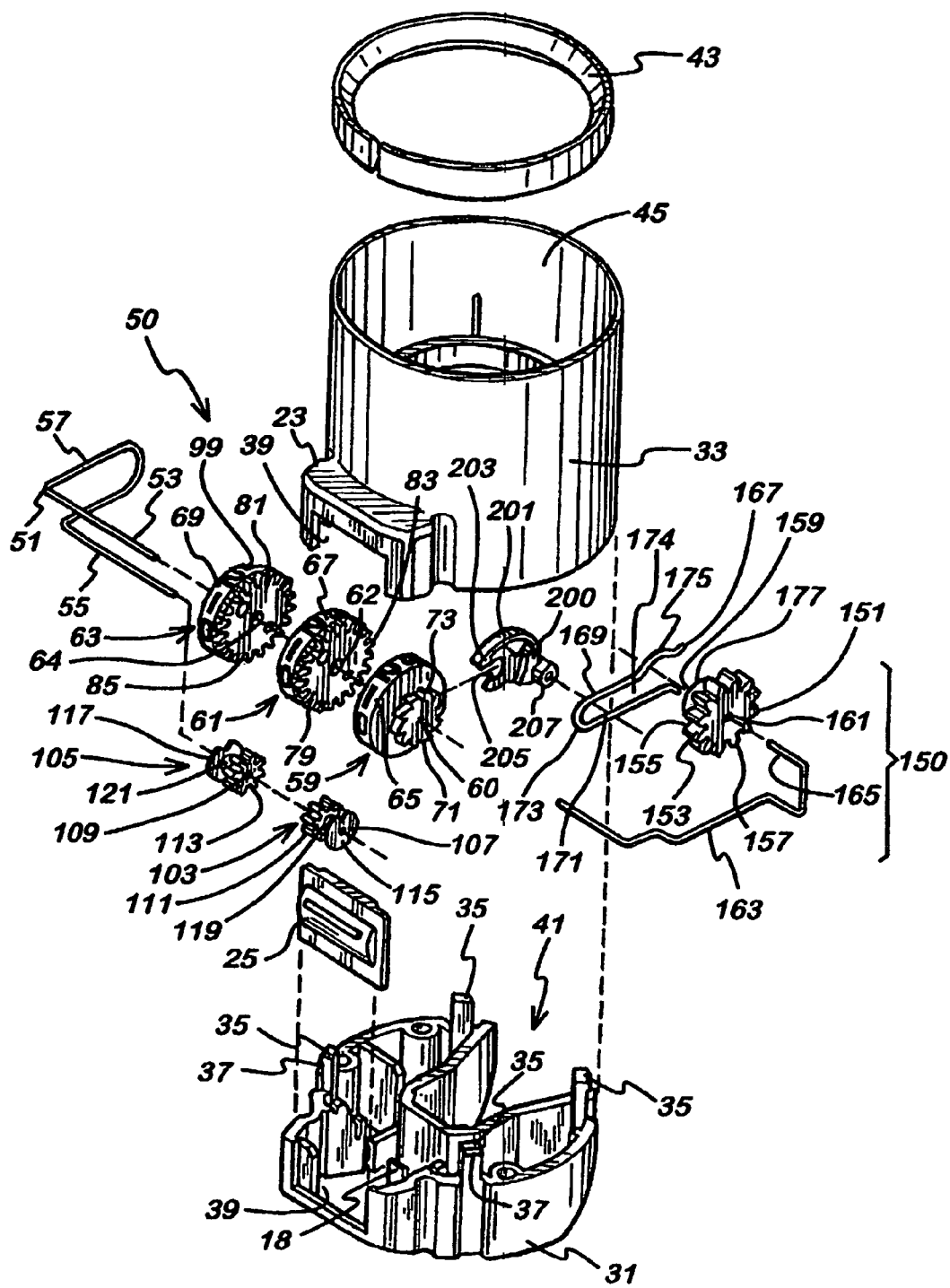
FIG. 2 is an exploded perspective view of the dose counter module.

FIG. 1 shows a pressurised metered dose inhaler, or pMDI, 1. The pMDI 1 comprises a tubular actuator 3 of a generally L-shape. The actuator 3 is provided with an open-ended through passage or internal passageway 5 which extends from an upper opening or open end 7 to a lower opening (not shown) in a mouthpiece 9. The actuator further comprises a viewing window 11.

The pMDI 1 further comprises an aerosol canister unit 15, which comprises an aerosol canister 17, shown in ghost and having a standard construction as described in the 'Background of the Invention' section above, and a dose counter module 19 mounted on the outlet end of the canister 17. The aerosol canister 17 contains a pressurised medicinal aerosol formulation, for example a therapeutic agent suspended or dissolved in a liquified gas propellant, typically a hydrofluoroalkane (HFA) propellant, such as HFA-134a or HFA-227.

As will be understood from the 'Background of the Invention' section above, the aerosol canister unit 15 is adapted to be slid into the passageway 5 of the actuator 3 through the upper opening 7 when the aerosol canister unit 15 is inverted, i.e. with the dose counter module 19 at the leading end, so that it is inserted first into the actuator 3.

The aerosol canister unit 15 is slid along the passageway 5 to a rest position in which a dispensing member (not shown) of the aerosol canister 17, which projects into the dose counter module 19, engages a stand (not shown) in the passageway 5 so that the dispensing member is held stationary in the actuator 3. Further depression of the aerosol canister unit 15 into the passageway 5 causes the dispensing member to be depressed into the aerosol canister 17 and a metered dose of the medicinal aerosol formulation will then be dispensed from the aerosol canister 17. The dose will thereby be exhausted from the actuator 3 through the mouthpiece 9.

For correct angular orientation of the aerosol canister unit 15 in the actuator 3, the passageway 5 defines a longitudinal inner track portion 21 to receive a complementary protrusion 23 on the outer circumferential surface of the dose counter module 19. The protrusion coincides with a display window 25 of the dose counter module. The window 11 of the actuator 3 is located in the wall of the longitudinal track portion 21 to ensure that the display window 25 on the protrusion 23 registers with the window 11 of the actuator 3. A patient can thereby view the display in the dose counter window 25 when the aerosol canister unit 15 is mounted in the actuator 3.

Referring to FIGS. 1 and 2, the dose counter module 19 has a hollow outer casing 30 made from a plastics material, for example polypropylene (PP). As shown in FIG. 2, the outer casing 30 is formed from a cap part 31 and a sleeve part 33. The cap part 31 has a plurality of posts 35 which project upwardly (in inverted orientation) from the periphery of the cap part 31. They are provided to extend through alignment holes (not shown) in the sleeve part 33. The posts 35 are subsequently joined or adhered to an inner surface of the sleeve part 33, for example by welding, such as ultrasonic welding. This ensures a permanent connection of the cap part 31 to the sleeve part 33.

The cap and sleeve parts 31,33 both comprise elements of the protrusion 23 of the dose counter module 19. The window 25 is retained in a track 39 formed in those elements of the protrusion 23 when the cap and sleeve parts 31, 33 are mated together. The window may be made of a transparent plastics material, for instance polymethyl methacrylate (PMMA), such as PERSPEX (RTM).

As shown in FIGS. 2 to 6, the cap part 31 has a generally U-shape cross section. When the dose counter module 19 is mounted to the outlet end of the aerosol canister 17, the dispensing member (not shown) of the aerosol canister 17 is received in the concave cut-out 41 of the U-shaped cap part 31. Moreover, when the aerosol canister unit 15 is slid into the actuator 3 to its rest position, the stand is received in the cut-out 41 for engagement with the dispensing member. In other words, the cap part 31 of the dose counter module 19 is arranged about the stand. See WO98/56444, and in particular FIG. 1 thereof, for a fuller disclosure of the dispensing member and the stand therefor.

Turning to FIG. 2, when the dose counter module 19 is assembled, it is mounted to the outlet end of the aerosol canister 17 through a split-ring collar 43, for example made of PP, which is mounted to the neck on the can of the aerosol canister 17 and then wedged between the neck and an inner circumferential surface 45 of the sleeve part 33 of the outer casing 30 prior to welding it thereto by ultrasonic welding, as further detailed in WO-A-0128887, supra.

The outer casing 30 of the dose counter module 19 houses a mechanical dose counting mechanism, details of which now follow.

As shown in FIG. 4, the cap part 31 of the outer casing 30 retains a drums sub-assembly 50 of the counting mechanism. Referring also to FIG. 2, the drums sub-assembly 50 comprises an axle spring 51 having an upper axle 53, a lower axle 55, which extends parallel to the upper axle 53, and a U-shaped connector section 57 oriented perpendicularly to the upper and lower axles 53,55. The axle spring 51 is made from a metal, such as a stainless spring steel. The connector section 57 operates to bias the upper and lower axles 53,55 to a closed position, i.e. towards one another.

The drums sub-assembly 50 further comprises a set of three indicator wheels 59,61,63 which are adapted to be co-axially mounted on the upper axle 53 for rotation thereon. The indicator wheels 59,61,63 are formed from a plastics material, e.g. acetal, ideally by injection moulding. Each indicator wheel 59,61,63 is provided with a central aperture 60,62,64 to enable them to be slid onto the upper axle 53 of the axle spring 51.

Each indicator wheel 59,61,63 has numbers arranged circumferentially in order on the rims 65,67,69 of the wheels 59,61,63, applied for example in the manner disclosed in International patent application publication WO-A-0108733, also to Glaxo Group Limited.

The rotational position of each indicator wheel 59,61,63 on the upper axle 53 determines which number on its rim 65,67, 69 is displayed through the window 25 of the dose counter module 19. The indicator wheels 59,61,63 collectively display a three digit number in the window 25, which number identifies the number of metered doses of the medicinal aerosol formulation left in the aerosol canister 17. Thus, at the outset, i.e. before use, the indicator wheels 59,61,63 are arranged on the upper axle 53 so that the three digit number displayed in the window 25 corresponds to the label claim of metered doses available in the aerosol canister 17.

It is convenient to refer to the right-hand indicator wheel 59 (as viewed in e.g. FIG. 7) as the "units wheel", the central indicator wheel 61 as the "tens wheel" and the left-hand indicator wheel 63 as the "hundreds wheel" because the numbers displayed thereon correspond to the units, tens and hundreds of the dose count displayed in the window 25.

It will be appreciated that the use of three indicator wheels 59,61,63 enables the dose counter module 19 to be used with an aerosol canister which is filled with over one hundred metered doses of a medicinal aerosol formulation. As will be understood, the number of indicator wheels could be increased or decreased depending on the number of metered doses in the aerosol canister 17. For instance, if the "label claim" was less than a hundred metered doses, it may be convenient to use only two indicator wheels. Of course, three indicator wheels could still be used.

In this embodiment, the units and tens wheels 59,61 each have the numbers '0' to '9' inclusive equi-angularly arranged thereon in series, while the hundreds wheel 63 only has the numbers '0' to '2' inclusive arranged thereon in series, although with the same inter-number angular spacing (36°) as for the numbers on the units and tens wheels 59,61. Of course, the series of numbers on the hundreds wheel 63 can be increased or decreased, depending on the "start count" desired.

Figure 5:
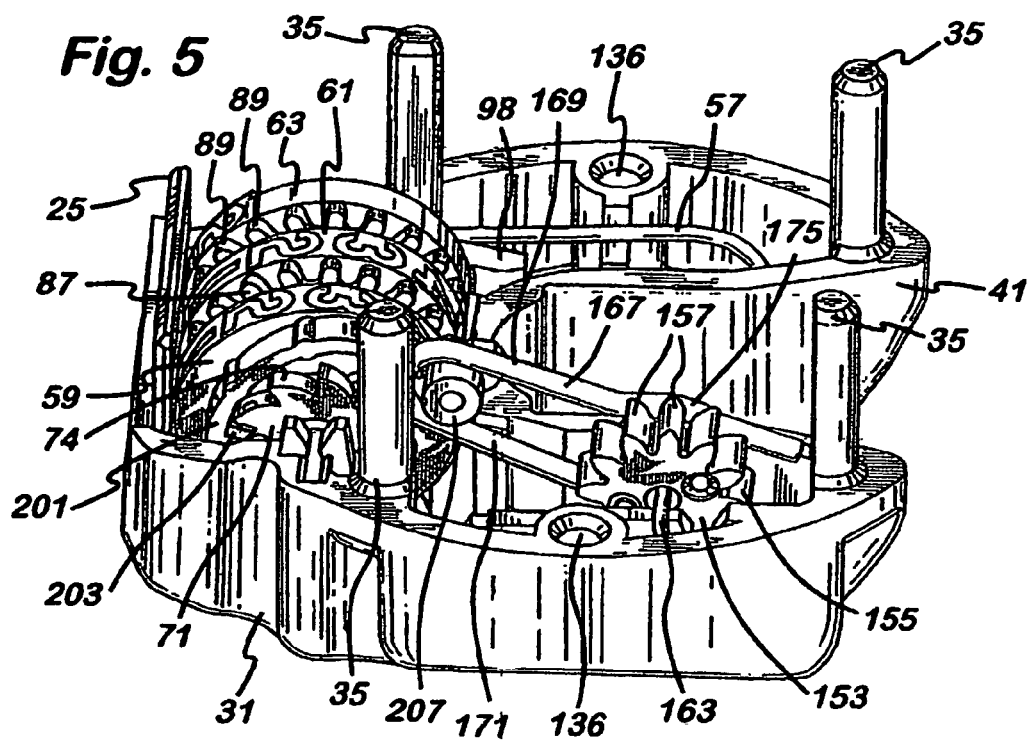
FIG. 5 is a second perspective view of the cap part from an opposite direction to that of FIG. 4, with a clutch spring fitted thereto.
Figure 7:
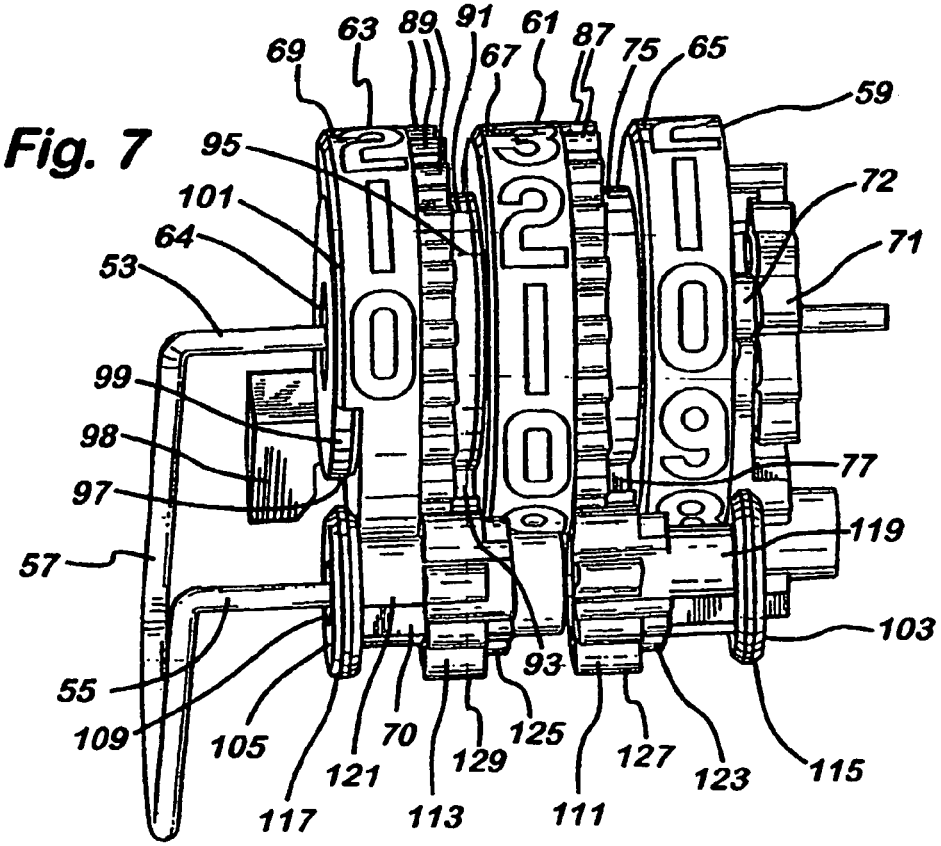
FIG. 7 is a perspective front view of the drums sub-assembly.
Figure 14A:
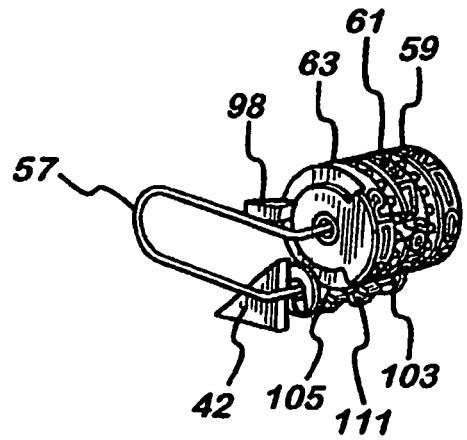
FIGS. 14A-F are a series of views illustrating how the knock gears of the drums sub-assembly transmit rotation from one drum to another to decrement the number displayed by the drums sub-assembly.
Figure 14B:
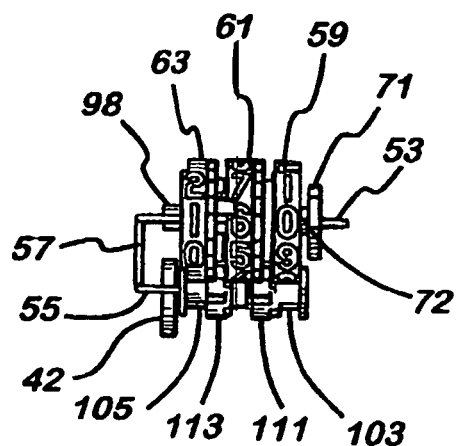
Figure 14C:
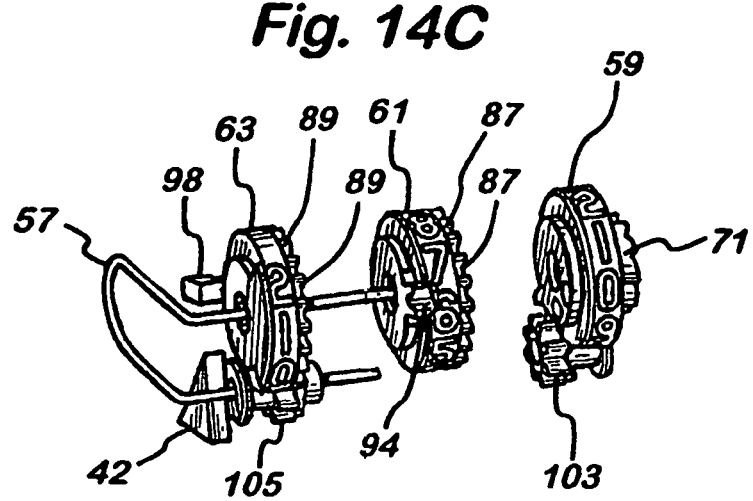
Figure 14D:
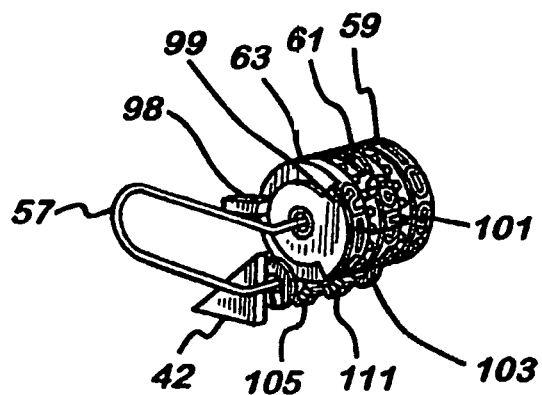
Figure 14E:
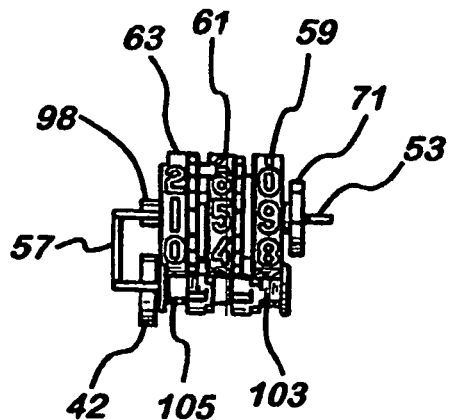
Figure 14F:
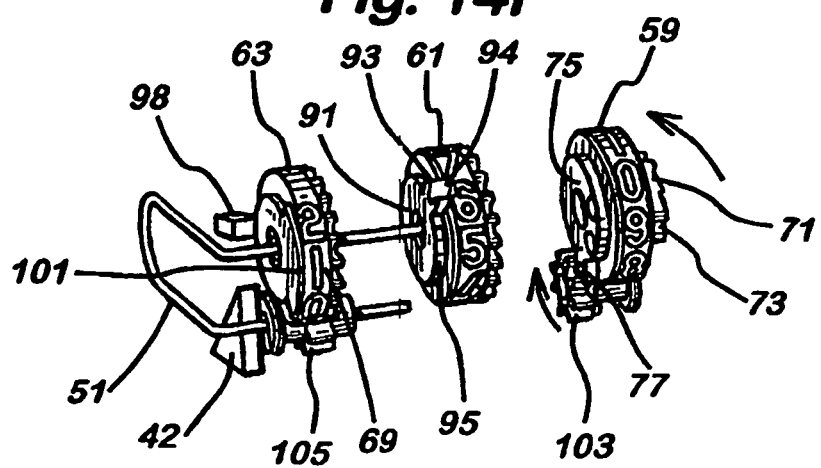
Figure 15A:
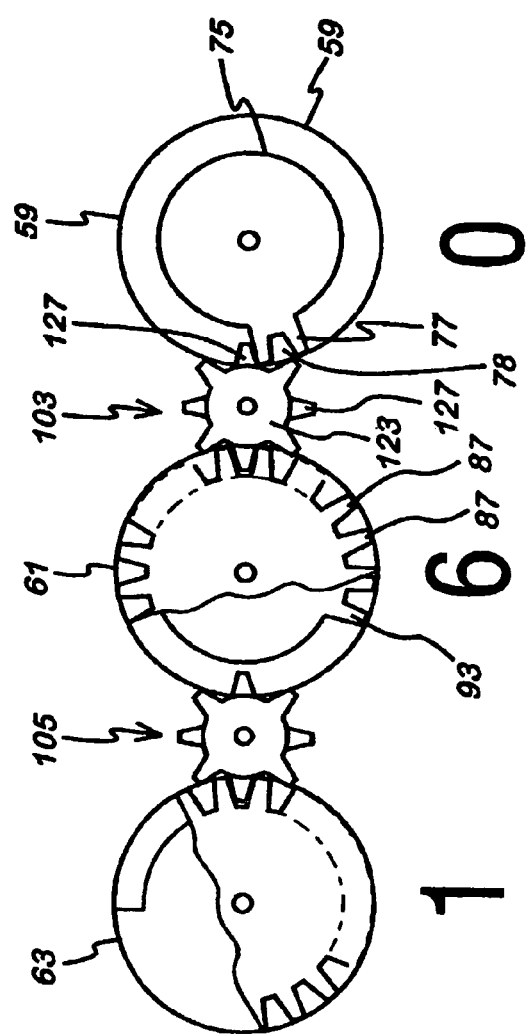
FIGS. 15A-B are schematic views illustrating the operation of the knock gears.
Figure 15B:
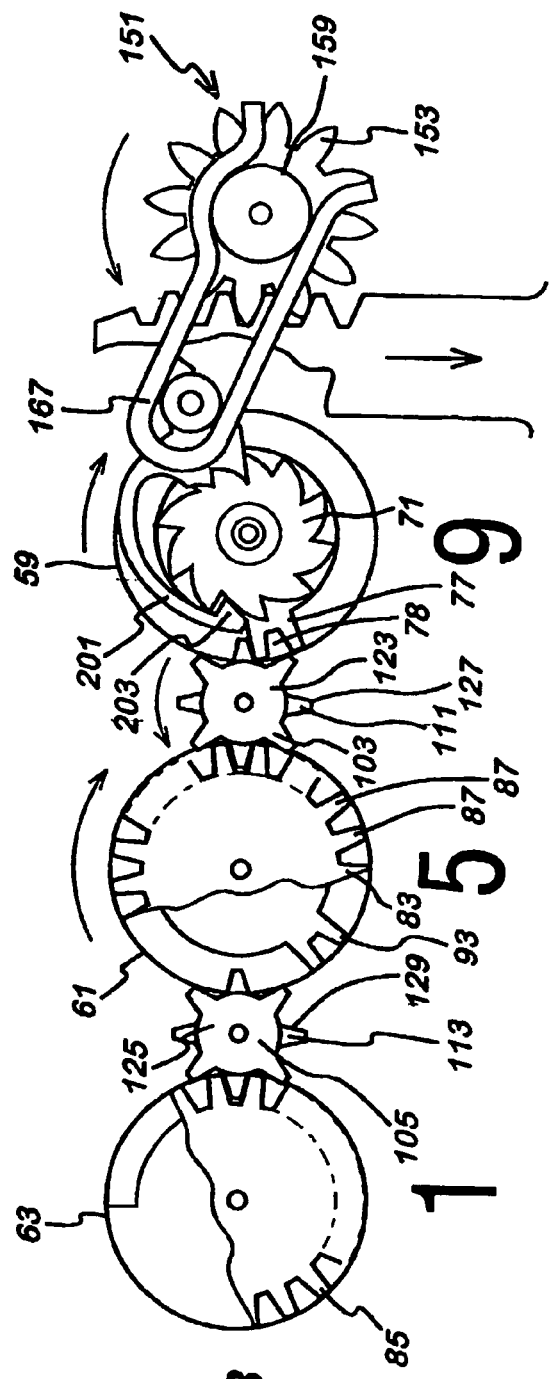

As shown in FIGS. 2 and 5, the units wheel 59 has a ratchet wheel 71 on its right-hand side which is provided with teeth 74 on its circumference 73. The ratchet wheel 71 is supported on the end of a shaft 72 (see FIGS. 7 and 14B). Referring now to FIGS. 7, 14F and 15A, the left-hand side of the units wheel 59 is provided with a boss 75 provided with just two teeth (a "bunny" tooth 77). As shown in FIG. 2, the tens wheel 61 and the hundreds wheel 63 each have a boss 79,81 on the right-hand side with a toothed circumference 83,85. FIG. 7 shows that the toothed circumferences 83,85 have teeth 87,89 whose tips are flush with the rims 67,69 of the associated indicator wheel 61,63. As shown in FIGS. 7 and 14F, the tens wheel 61 is further provided with a boss 91 on its left-hand side which is also provided with a bunny tooth 93 on its outer circumference 95.

As further shown in FIGS. 7 and 14F, as well as FIG. 4, the hundreds wheel 63 has a boss 97 having an outer circumference 99 provided with a radially protruding segment 101 which lies flush with the rim 69 of the hundreds wheel 63.

Referring to FIG. 2, the drums sub-assembly 50 further comprises a set of two knock gears 103,105 having axial apertures 107,109 which enable the knock gears 103,105 to be co-axially mounted on the lower axle 55 of the axle spring 51 for rotation thereon. As shown in FIG. 7, for example, each knock gear 103,105 has a toothed wheel portion 111,113, a disc portion 115,117 arranged parallel to the associated toothed wheeled portion 111,113, but axially offset therefrom, and an axially-arranged hollow shaft portion 119,121 which connects the associated toothed wheel and disc portions 111,113:115,117. The knock gears are made of a plastics material, e.g. acetal, and are ideally made by injection moulding.

The disc portions 115,117 of the knock gears 103,105 function to locate the knock gears and indicator wheels correctly in the cap part 31. In particular, the disc portions 115, 117 inhibit axial play of the indicator wheels and knock gears on the axle spring 51 by overlapping the outer surfaces of the units and hundreds wheels 59,63, on the one hand, and being overlapped by surface features in the cap part 31 (not shown), on the other hand. So, neither the indicator wheels 59,61,63 nor the knock gears 103,105 can be outwardly axially displaced on the spring axle 51 once located in the outer casing 30.

As further shown in FIG. 7, the toothed wheeled portions 111,113 of the knock gears 103,105 are divided into two axial sections, a right-hand side section 123,125 and a left-hand side section 127,129. The number of teeth presented by the right-hand side sections 123,125 (4 teeth) is less than the number of teeth presented by the left-hand side sections 127, 129.

As will be understood from FIG. 7, when the indicator wheels 59,61,63 and knock gears 103,105 are mounted on the upper and lower axles 53,55, respectively, the rims 65,67 of the units and tens wheels 59,61 are rotatably supported between adjacent teeth in the right-hand side sections 123, 125 of the toothed wheeled portions 111,113 of the knock gears 103,105. Moreover, the teeth 87,89 on the tens wheel 61 and the hundreds wheel 63 mesh with the teeth of the left-hand side sections 127,129 of the toothed wheel portions 111,113 of the knock gears 103,105.

As will be further understood from FIG. 7, for example, the inherent biasing force in the axle spring 51 ensures that the indicator wheels 59,61,63 and knock gears 103,105 are biased towards one another so that the interengagable circumferential surfaces thereof interengage one another. In other words, the upper and lower axles 53,55 need to be parted against the action of the biasing force to accommodate the indicator wheels 59,61,63 and knock gears 103,105. Thus, in the assembled state of the drums sub-assembly 50, the upper and lower axles 53,55 are spaced apart by a distance which is greater than their spacing in the rest or return state of the axle spring 51. Accordingly, the upper and lower axles 53,55 push the indicator wheels 59,61,63 and knock gears 103,105, respectively, towards one another. A good connection between the indicator wheels 59,61,63 and knock gears 103, 105 therefore results.

Also mountable in the cap part 31 of the outer casing 30 of the dose counter module 19 is a drive wheel sub-assembly 150 of the counting mechanism. Referring to FIG. 2 to 6, the drive wheel sub-assembly 150 comprises a drive wheel 151 having a pinion 153 having an outer circumference 155 defined by a series of teeth 157. The drive wheel 151 further comprises a boss 159 extending axially from the left-hand side of the pinion 153 (as viewed in e.g. FIG. 2). An axial passage or passageway 161 extends through the pinion 153 and the boss 159.

The drive wheel 151 is a plastics component of the dose counter module 19, e.g. of acetal, for instance made by injection moulding. The drive wheel sub-assembly 150 further comprises a drive wheel support spring 163 made from a metal, such as stainless steel. The drive wheel support spring 163 defines an axle section 165 which is insertable into the axial passageway 161 of the drive wheel 151 for rotatable support of the drive wheel 151.

The drive wheel sub-assembly 150 yet further comprises a slipping clutch spring 167, preferably formed from a metal, such as stainless spring steel. The clutch spring 167 is of a generally U-shaped configuration having a pair of generally parallel arm sections 169,171 connected by a U-bend connector section 173. The connector section 173 biases the arm sections 169,171 to be closed together thereby enabling the arm sections 169,171 to be clamped onto the boss 159 of the drive wheel 151, as shown in FIG. 9, for example. More particularly, one of the arm sections 169 of the clutch spring 167 is formed with a curved portion 175 adjacent its free end which is of complementary size and shape to the outer circumferential surface 177 of the boss 159.

Thus, when the drive wheel 151 rotates on the axle section 165 of the drive wheel support spring 163, the clutch spring rotates therewith. However, if a sufficient force is applied to the clutch spring 167 which opposes its rotation with the drive wheel 151, the clutch spring 167 slips on the boss 159. Therefore, the rotation of the drive wheel 151 will not be transmitted to the slipping clutch spring 167.

FIG. 2 shows that the dose counting mechanism further comprises a rotatable plastics pawl 200 (e.g. acetal) having a pawl arm 201 with a pawl tooth 203 at its tip, a C-shaped hub 205 shaped to be rotatably mounted on the shaft 72 of the units wheel 59, and a boss 207 extending axially from the right-hand side of the rotatable pawl 200 which is adapted to be slidingly received in the track 174 defined between the arm sections 169,171 of the clutch spring 167. The pawl may be injection moulded.

The assembled state of the counting mechanism is shown in FIG. 7, and its arrangement in the cap part 31 of the outer casing 30 of the dose counter module 19 is shown in FIGS. 4-6. The operation of the counting mechanism to show the number of metered doses of the medicinal aerosol formulation left will now be described.

When the aerosol canister unit 15 is in its rest position in the actuator 3, the counting mechanism of the dose counter module 19 is in the state shown in FIGS. 8, 9 and 10A-B. More particularly, a rack 13 projecting upwardly from a base surface of the actuator 3 extends through an aperture 20 in the cap part 31 of the outer casing 30 of the dose counter module 19 so that a set of teeth 14 on the rack 13 mesh with the teeth 157 of the pinion 153 of the drive wheel 151. In this regard, the drive wheel support spring 163 biases the drive wheel 151 towards the window 25. The interaction of the rack 13 with the pinion 153 causes the drive wheel 151 to be displaced against the biasing force of the drive wheel support spring 163. This results in the pinion teeth 157 being biased against the rack teeth 14 thereby ensuring a good engagement therebetween.

In the rest position of the aerosol canister unit 15 in the actuator 3, the rotatable pawl 200 has an angular orientation relative to the ratchet wheel 71 which results in the pawl tooth 203 engaging behind one of the ratchet teeth 74.

If the aerosol canister unit 15 has been previously unused, the indicator wheels 59,61,63 are arranged on the upper axle 53 of the axle spring 51 so that the numerical indicia thereon are lined up to show in the window 25 of the actuator 3 the starting number of metered doses available in the aerosol canister 17 for dispensing. This starting number corresponds to the number of metered doses stated on the label of the aerosol canister 17, e.g. the "label claim". As an example, the starting number of metered doses may be '160', as indicated in FIG. 15A. The label claim need not, however, match the actual number of available doses since an aerosol canister will usually be overfilled slightly to allow for losses during storage, for example. This also provides a reserve of doses for a user once the counter has reached zero in case of emergencies.

Figure 10A:
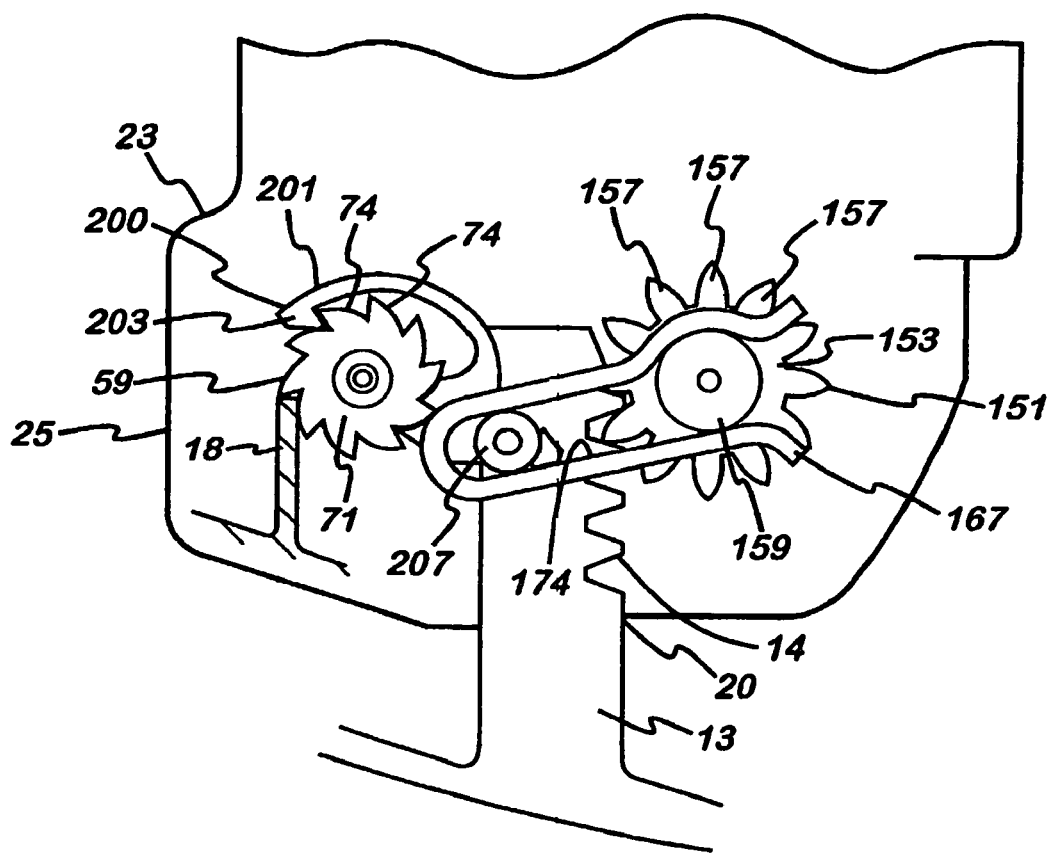
FIGS. 10 to 13 are schematic views showing the sequence of steps by which the drive wheel sub-assembly drives the drums sub-assembly.
Figure 10B:
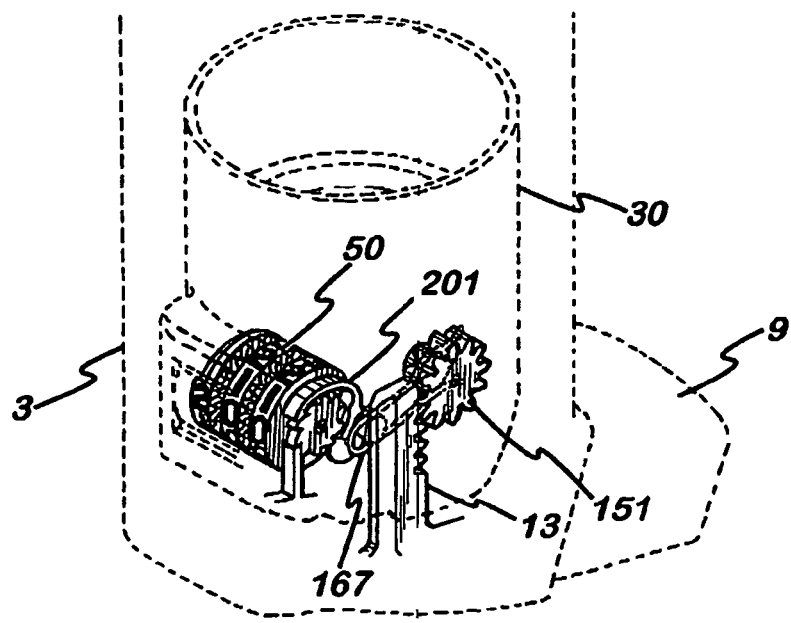
Figure 11B:
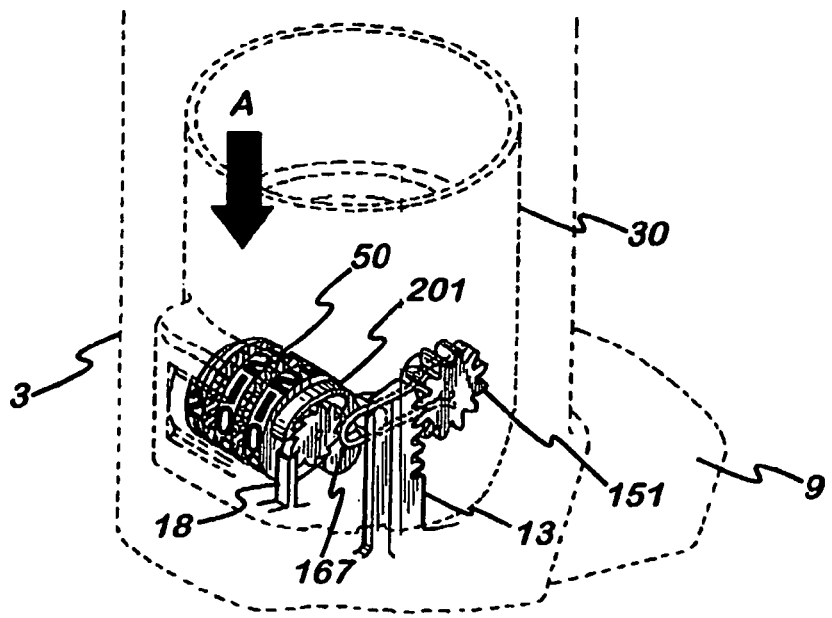
Figure 12A:
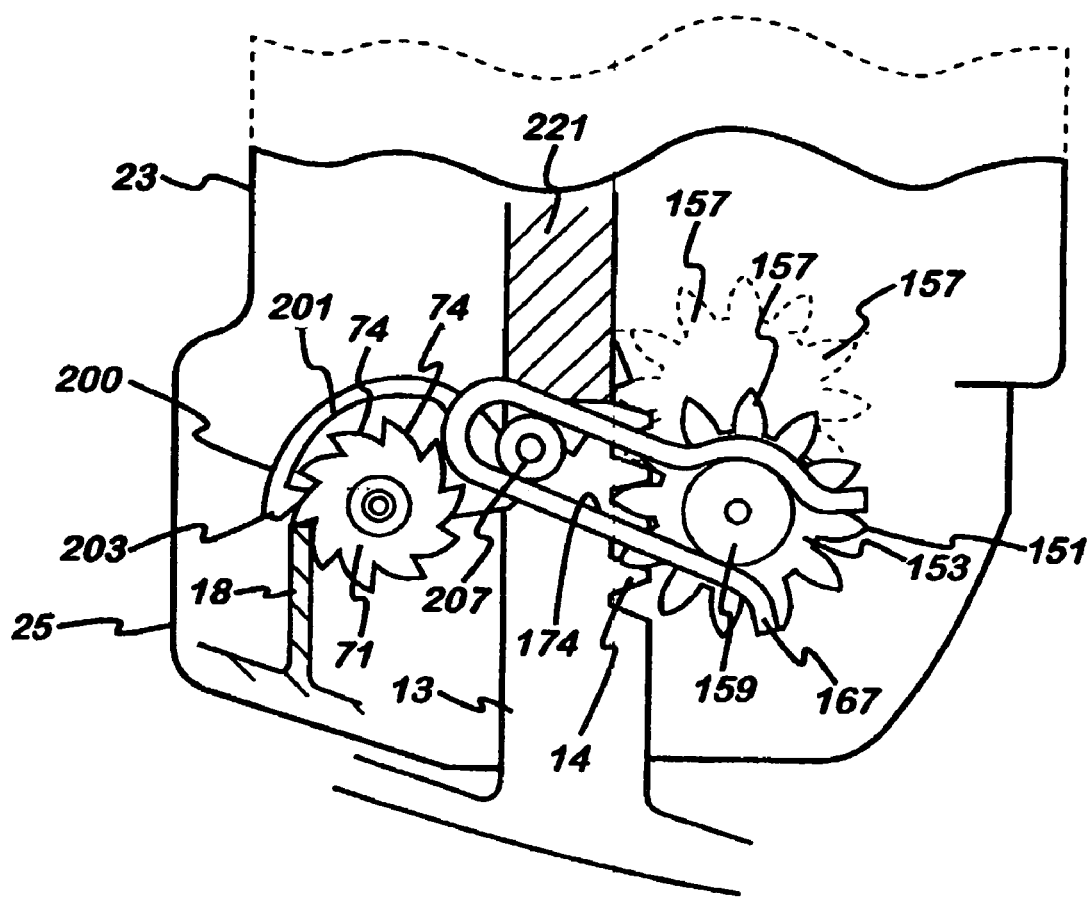
Figure 12B:
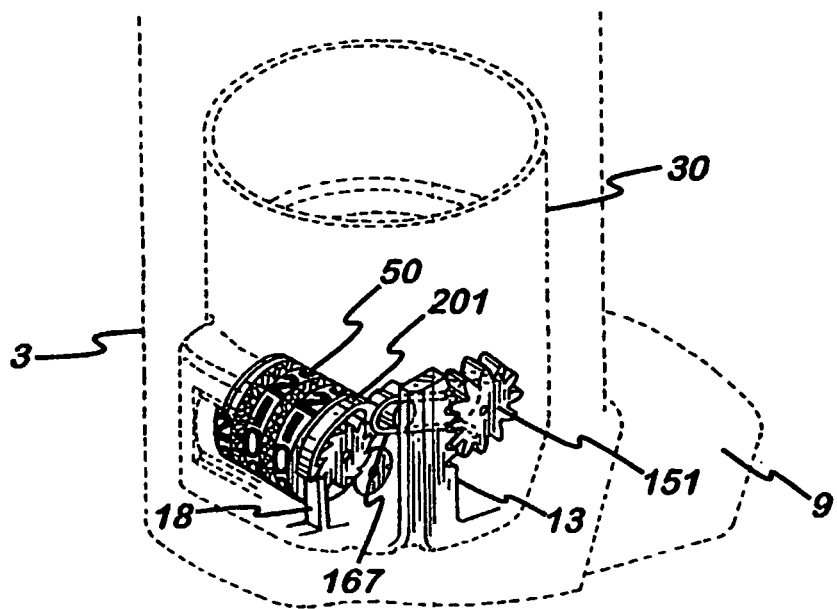
Figure 13B:
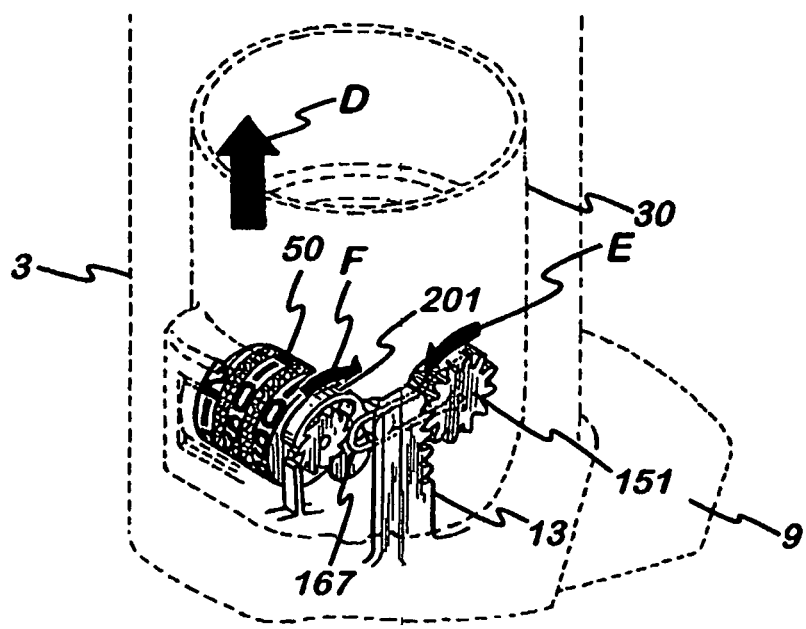

When a patient wishes to dispense a metered dose of the aerosol formulation, the patient places their lips on the mouthpiece 9 of the actuator 3 then simultaneously inhales and depresses the aerosol canister unit 15 into the actuator 3. The start of this downstroke of the aerosol canister unit 15 into the actuator 3 is shown in FIGS. 11A-B. In comparison FIGS. 10A-B shows the counting mechanism at rest.

The downstroke causes the dose counter module 19 to move downwardly in the direction of arrow A relative to the rack 13 of the actuator 3. This relative movement causes the teeth 14 of the rack 13 to rotate the drive wheel 151 in the direction of arrow B through its interaction with the pinion 153. The rotation of the drive wheel 151 causes the clutch spring 167 mounted on the boss 159 to rotate therewith. This in turn causes the rotatable pawl 200 to rotate on the shaft 72 of the units wheel 59 in the direction of arrow C, which direction is opposite to the direction of rotation B of the drive wheel 151.

As will be appreciated from FIG. 11A, the rotation of the pawl 200 in the direction of arrow C is caused through the location of the boss 207 of the pawl 200 in the guide track 174 defined in the clutch spring 167.

As will be further appreciated from FIG. 11A, the rotation of the pawl 200 in the direction of arrow C on the units wheel 59 causes the pawl arm 201 to disengage from behind the trailing surface of the ratchet tooth 74 it was engaged with in the rest position, and to slide up the leading flank surface of the next adjacent ratchet tooth 74.

Continued depression of the aerosol canister unit 15 into the actuator 3 causes the valve thereof to open, and for a metered dose of the medicinal aerosol formulation to be discharged from the mouthpiece 9, generally, in use, into the respiratory tract of the patient. As shown in FIG. 12A, the rotation of the pawl 200 on the units wheel 59 is continued until the pawl tooth 203 drops behind the trailing flank surface of the next adjacent ratchet tooth 74. From this it will be appreciated that the pawl arm 201 is a resilient arm whereby the pawl tooth 203 at the free end thereof falls from the tip of one ratchet tooth 74 to the leading flank surface of the next adjacent ratchet tooth during the downstroke.

The rotation of the pawl 200 on the units drum 59 is not transmitted thereto due to a fixed pawl or resilient non-return leg 18 in the cap part 31 of the outer casing 30 of the dose counter module 19 engaging behind the trailing flank surface of one of the ratchet teeth 74 of the ratchet wheel 71 of the units wheel 59.

Comparison of FIG. 12A to FIG. 11A shows that the rotation of the pinion 153 of the drive wheel 151 is able to be translated into counter-rotation of the pawl 200 on the units wheel 59 through the ability of the boss 207 of the pawl 200 to slide in the guide track 174 defined in the clutch spring 167. In other words, there is a "toggle link"-type coupling between the drive wheel 151 and the pawl 200.

As further shown in FIG. 12A, when the rack 13 causes the pinion 153 to rotate the drive wheel 151 a predetermined angle, the pawl 200 abuts with an end stop 221 which extends downwardly from the sleeve part 33 of the outer casing 30 of the dose counter module 19. This prevents the pawl 200 over-rotating on the units wheel 59 and the pawl tooth 203 being indexed over more than one ratchet tooth 74 on the downstroke of the aerosol canister unit 15. Once the pawl 200 bears against the end stop 221, continued depression of the aerosol canister unit 15 into the actuator 3 (e.g. to open the valve) is accommodated by the clutch spring 167 slipping on the boss 159 of the drive wheel 151 (as a result of the clutch spring 167 only being retained thereon by friction forces). That is to say, the drive wheel 151 is free to continue rotating once the pawl 200 abuts with the end stop 221 without this rotation being transmitted to the pawl 200 due to the drive wheel 151 rotating relative to the clutch spring 167, i.e. there is a lost motion coupling.

Once the aerosol canister unit 15 has been depressed to the bottom of its downstroke, and a metered dose of the medicinal aerosol formulation released, the patient releases, or reduces, the downward pressure on the aerosol canister unit 15 whereupon the biasing mechanism in the valve assembly of the aerosol canister 17 biases the aerosol canister unit 15 back towards its rest position. The return stroke of the aerosol canister unit 15 in the actuator 3 is shown schematically in FIGS. 13A-B.

As shown, as the aerosol canister unit 15 is translated upwardly in the direction of arrow D, the engagement of the rack 13 with the pinion 153 causes the drive wheel 151 to rotate in an opposite direction (arrow E). The toggle-link coupling between the drive wheel 151 and pawl 200 causes the pawl 200 to rotate in an opposite direction (arrow F). The rotation of the pawl 200 in the direction of arrow F causes the pawl arm 201 to pull the units wheel 59 in the same direction through the engagement of the pawl tooth 203 with the trailing flank surface of the ratchet tooth 74 which it dropped over on the downstroke of the aerosol canister unit 15 in the actuator 3. In this regard, the fixed pawl 18 is resiliently formed so that it is able to be flexed out of the way by one of the ratchet teeth 74 and then drop behind that tooth 74 to prevent counter-rotation of the units wheel 59 at the end of the return stroke of the aerosol canister unit 15 in the actuator 3.

As shown in FIG. 9, once the rack 13 has caused the drive wheel 151 to rotate a predetermined angular extent, the pawl 200 abuts with another end stop 66, this time presented by the cap part 31 of the outer casing 30. This prevents the pawl 200 causing more than one ratchet tooth 74 to pass the fixed pawl 18 on the return stroke of the aerosol canister unit 15. If at this stage the return stroke of the aerosol canister unit is incomplete, i.e. the rest position has not been reached, the drive wheel 151 is free to continue rotating relative to the slipping clutch spring 167 in the direction of arrow E (through the engagement of the rack 13 with the pinion 153).

The result of the rotation of the units wheel 59 in the direction of arrow F is to cause the numerical indicia it displays in the window 25 to be decreased by one, thereby indicating to the patient that there is now one less metered dose left in the aerosol canister 17.

Thus, upon each actuation cycle of the aerosol canister unit 15, the units wheel 59 is caused to be rotatably indexed by an angular amount sufficient to cause the previous units figure displayed in the window 25 to be advanced and replaced by the next unit figure in the series, which is one less than the previous figure. Bearing in mind that the numerical indicia on the units wheel 59 are equi-angularly spaced about the circumference thereof, the units wheel 59 is rotatively indexed by 36° upon each actuation cycle of the aerosol canister unit 15. It will thus be appreciated that the number of ratchet teeth 74 on the ratchet wheel 71 corresponds to the number of numerical indicia on the units wheel 59, i.e. 10. It will further be appreciated that after each complete revolution of the units wheel 59 the same units figure is displayed in the window 25.

As the units wheel 59 is rotatively indexed by the pawl-and-ratchet mechanism, the bunny tooth 77 of the units wheel 59 will engage the left-hand side section 127 of the toothed wheel portion 111 of the right-hand knock gear 103 at the same point in each revolution of the units wheel 59 on the upper axle 53. As indicated in FIG. 15A, the bunny tooth 77 is arranged on the units wheel 59 so that its engagement with the left-hand side section 127 of the toothed wheel portion 111 of the right-hand knock gear 103 coincides with the number '0' being displayed by the units wheel 59 in the window 25. The next actuation cycle of the aerosol canister unit 15 causes the bunny tooth 77 to transmit a rotational force to the right-hand knock gear 103, through its engagement with the left-hand side section 127 of its toothed wheel portion 111. The rotation imparted to the right-hand knock gear 103 by the bunny tooth 77 of the units wheel 59 is transmitted to the tens wheel 61 through the meshing of the left-hand side section 127 of the toothed wheel portion 111 with the teeth 87 of the tens wheel 61. The net result of this is that the numerical indicia displayed by the units wheel 59 and tens wheel 61 are concurrently decremented by one. In the case shown in FIGS. 15A-B, the result is to decrement the number displayed in the window 25 from '160' to '159'. This is also illustrated in FIGS. 14A-F.

During the transmission of the rotational indexing of the units wheel 59 to the tens wheel 61 through the right-hand knock gear 103, the right-hand side section 123 of the toothed wheel portion 111 of the right-hand knock gear 103 is received in a recess 78 (FIG. 15A) formed in the rim 65 of the units wheel 59 which is co-extensive with the gap between the ears of the bunny tooth 77.

As the tens wheel 61 is incrementally driven by the units wheel 59 through the right-hand knock gear 103 at every complete rotation of the units wheel 59 (when the '0' decrements to '9'), the bunny tooth 93 on the tens wheel 61 is advanced towards engagement with the left-hand knock gear 105, specifically the left-hand side section 129 of the toothed wheel portion 113 thereof. As before, when the tens wheel 61 is angularly positioned so that it displays the figure '0' in the window 25 (at which point the units wheel 59 also displays its '0' figure in the window 25), the bunny tooth 93 is disposed adjacent a tooth of the left-hand side section 129 of the toothed wheel portion 113 of the left-hand knock gear 105. The result of the next actuation cycle of the aerosol canister unit 15 is to cause the rotation or motion imparted to the tens wheel 59, by the co-operation of the units wheel 59 and the right-hand knock gear 103, to be transmitted to the hundreds wheel 63 in likewise manner. This results in the numerical indicia displayed by the hundreds wheel 63 in the window 25 being decrement by one, whereby the full number displayed in the window by the drums sub-assembly 50 is decremented by one from a number which is a factor of one hundred, e.g. '100' to '099'.

As will be understood from FIGS. 8 and 14A-F, when the tens wheel 61 drives the hundreds wheel 63 through the left-hand knock gear 105, the right-hand side section 125 of the toothed wheel portion 113 of the left-hand knock gear 105 is received in a recess 94 in the rim 67 of the tens wheel 61 which is co-extensive with the space between the ears of the bunny tooth 93.

In addition to the features of the counting mechanism described above, the counting mechanism further comprises a "lockout" arrangement which locks the drums sub-assembly 50 from being driven when each indicator wheel 59,61,63 is angularly positioned on the upper axle 53 of the axle spring 51 so that the display reads '000'. However, the lockout arrangement is such as not to prevent the aerosol canister unit 15 still being able to be actuated to dispense doses of medicinal aerosol formulation still remaining in the aerosol canister 17. In this connection, as a matter of routine, medicinal aerosol canisters are overfilled (compared to the label claim) for safety issues. For example, for rescue medicaments, such as bronchodilators, it is imperative that the patient still be able to use the aerosol canister unit 15 after the label claim of metered doses has been used.

Figure 16A:
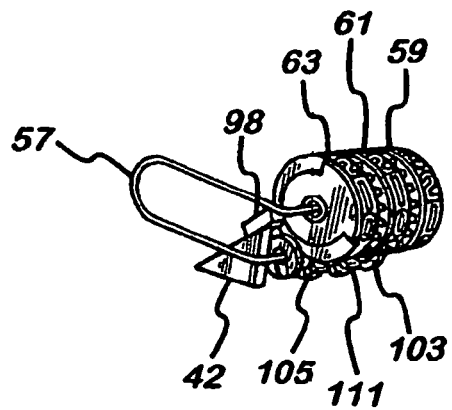
FIGS. 16A-F are a series of views illustrating how the drums sub-assembly reaches a "lockout" state in which the number displayed by the counter is not able to be advanced, while allowing continued actuation of the aerosol canister.
Figure 16B:
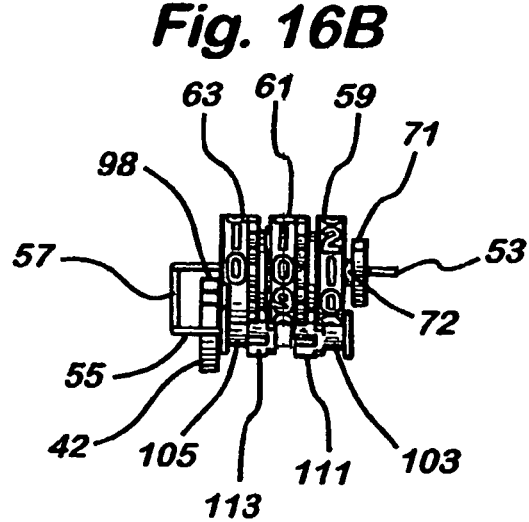
Figure 16C:
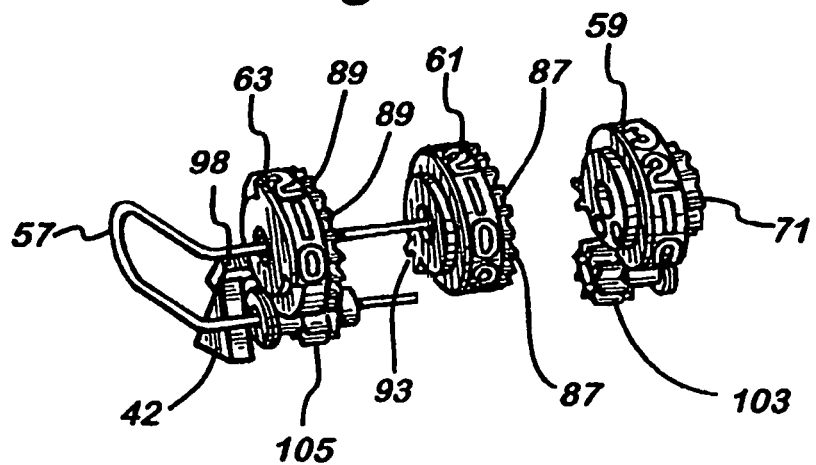
Figure 16D:
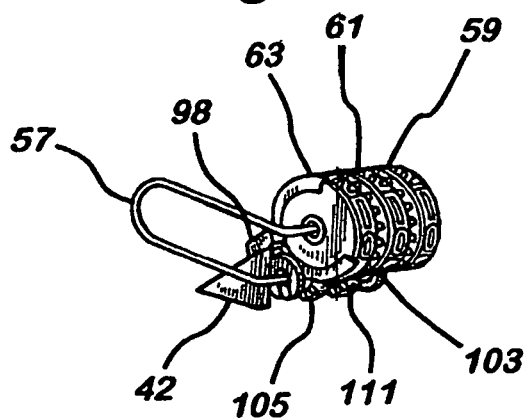
Figure 16E:
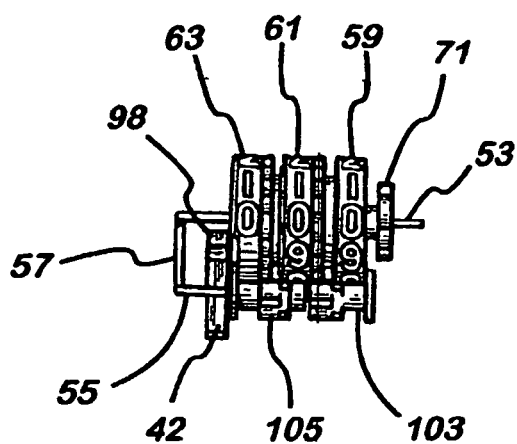
Figure 16F:
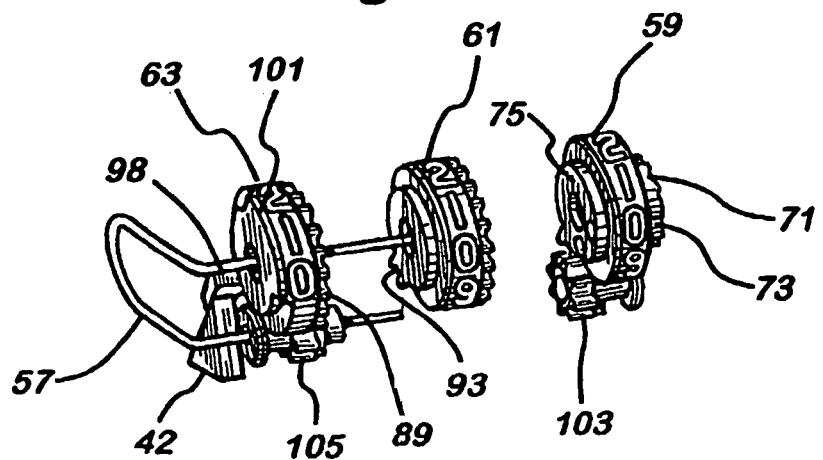
Figure 18:
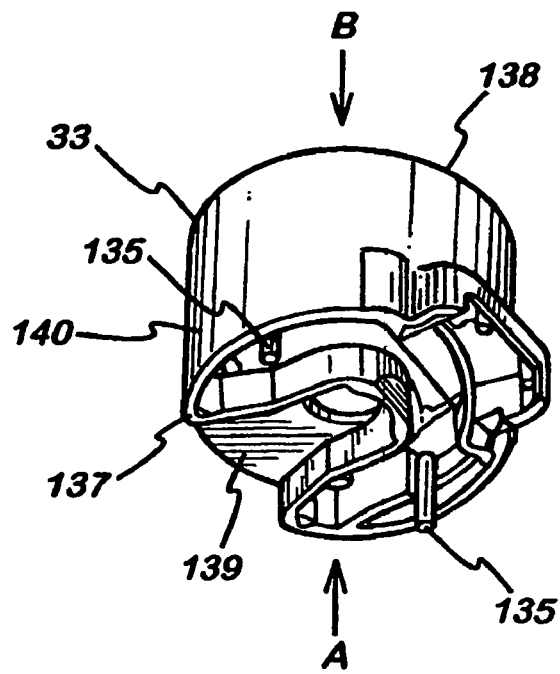
FIG. 18 is a perspective view of a sleeve part in accordance with the invention for a casing of a canister unit having a diameter of approximately 22 mm.
Figure 19:
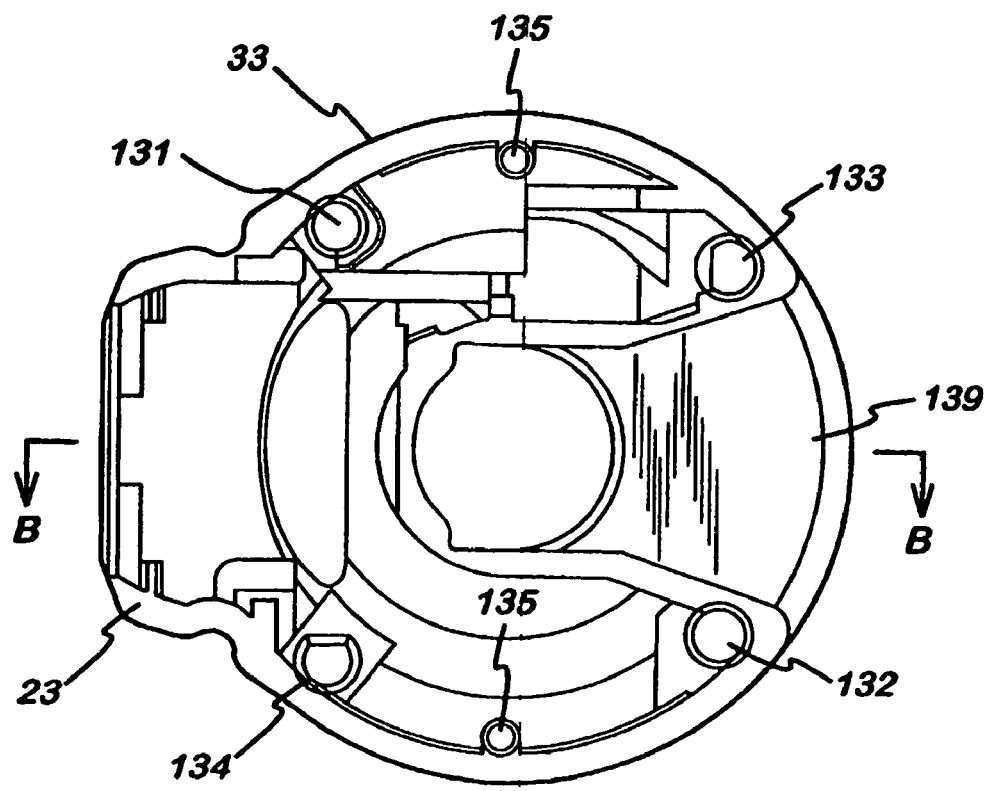
FIG. 19 is an end view of the sleeve part of FIG. 18 viewed in the direction of arrow A.
Figure 20:
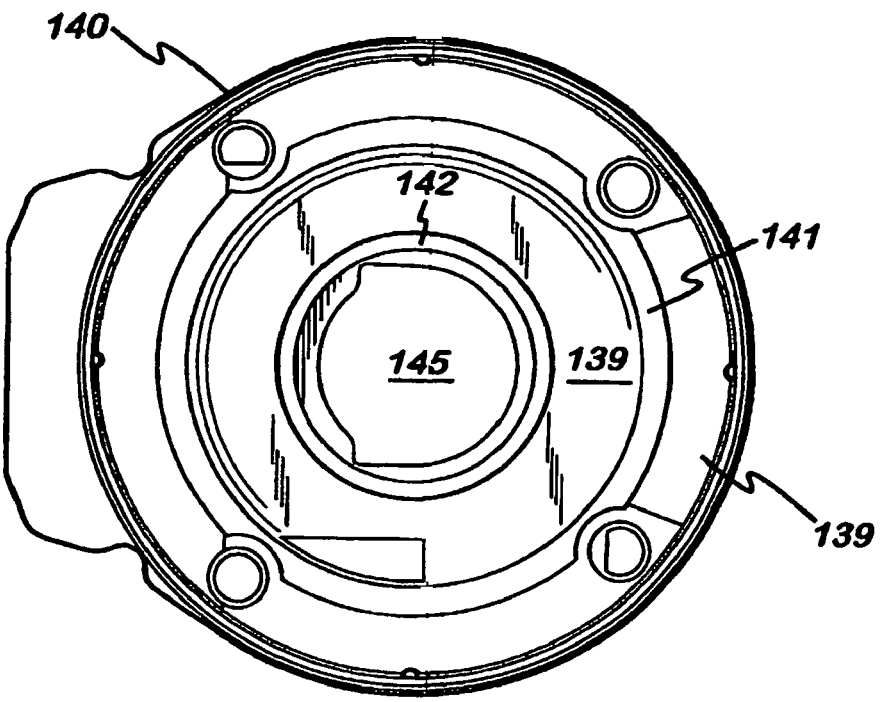
FIG. 20 is an end view of the sleeve part of FIG. 18 viewed in the direction of arrow B.
Figure 21:
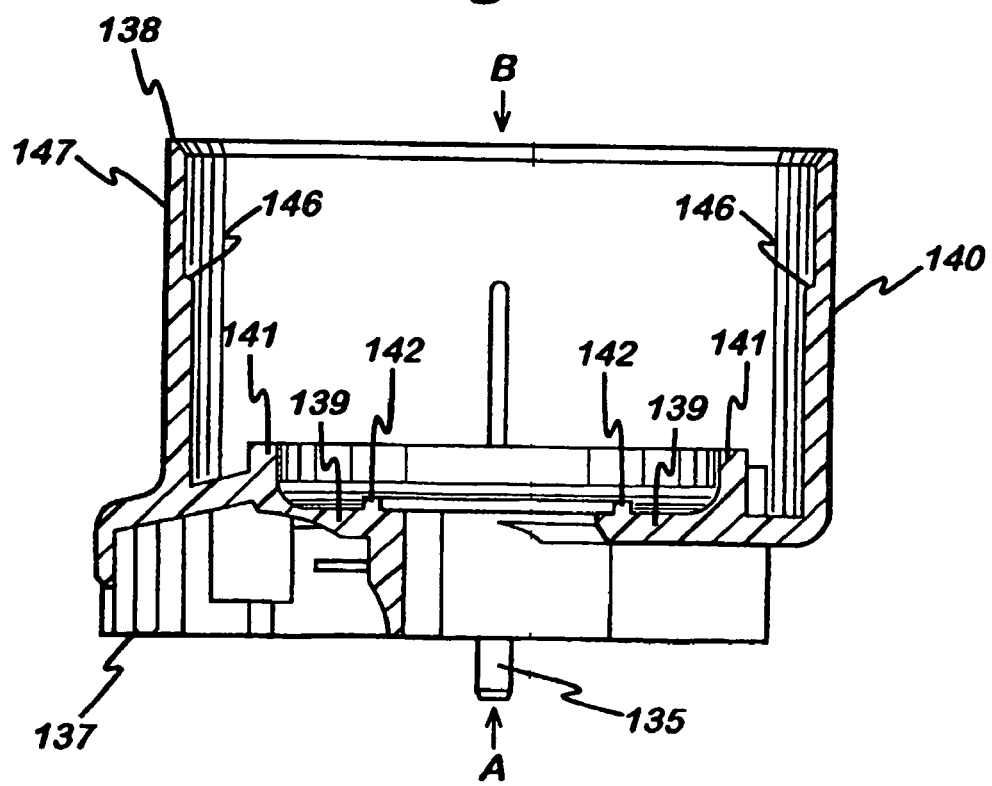
FIG. 21 is a section of the sleeve part through line B of FIG. 19.

Referring now to FIGS. 4, 16A and 17A, for example, the hundreds wheel 63 carries a peg 98 which, when the hundreds wheel 63 is angularly oriented so as to display a '0' in the window 25, abuts with a stop 42 provided in the cap part 31 of the outer casing 30 of the dose counter module 19. This abutment of the peg 98 with the stop 42 prevents further rotation of the hundreds wheel 63 by the pawl-and-ratchet drive mechanism. Moreover, the left-hand knock gear 105 is also locked from further rotation due to its interengagement with the locked hundreds wheel 63. So, once the hundreds wheel 63 has been locked by the abutment of the peg 98 with the stop 42, the tens wheel 61 is able to complete one further revolution on the upper axle 53 before it too becomes locked from further rotation through engagement of the bunny tooth 93 with the left-hand knock gear 105. The locking of the tens wheel 61 further results in the right-hand knock gear 103 being locked from further rotation due to its tooth engagement with the tens wheel 61. As will be understood, the tens wheel 61 becomes locked out when it too displays a '0' in the window 25.

Once the tens wheel 61 has been locked out, the units wheel 59 is able to complete just one more revolution for it to display a '0' in the window 25. The units wheel 59 then in turn becomes locked out by the interengagement of its bunny tooth 77 with the right-hand knock gear 103. See FIGS. 16A-F.

If a patient wishes to use the aerosol canister unit 17 after the drums sub-assembly 50 has been locked out, the actuation cycle is still able to be completed through the clutch spring 167 slipping on the boss 159 of the drive wheel 151. In other words, the drive system is disconnected from the drum sub-assembly 50 by the slipping clutch 167. This is shown schematically in FIG. 17B.

Figure 3:
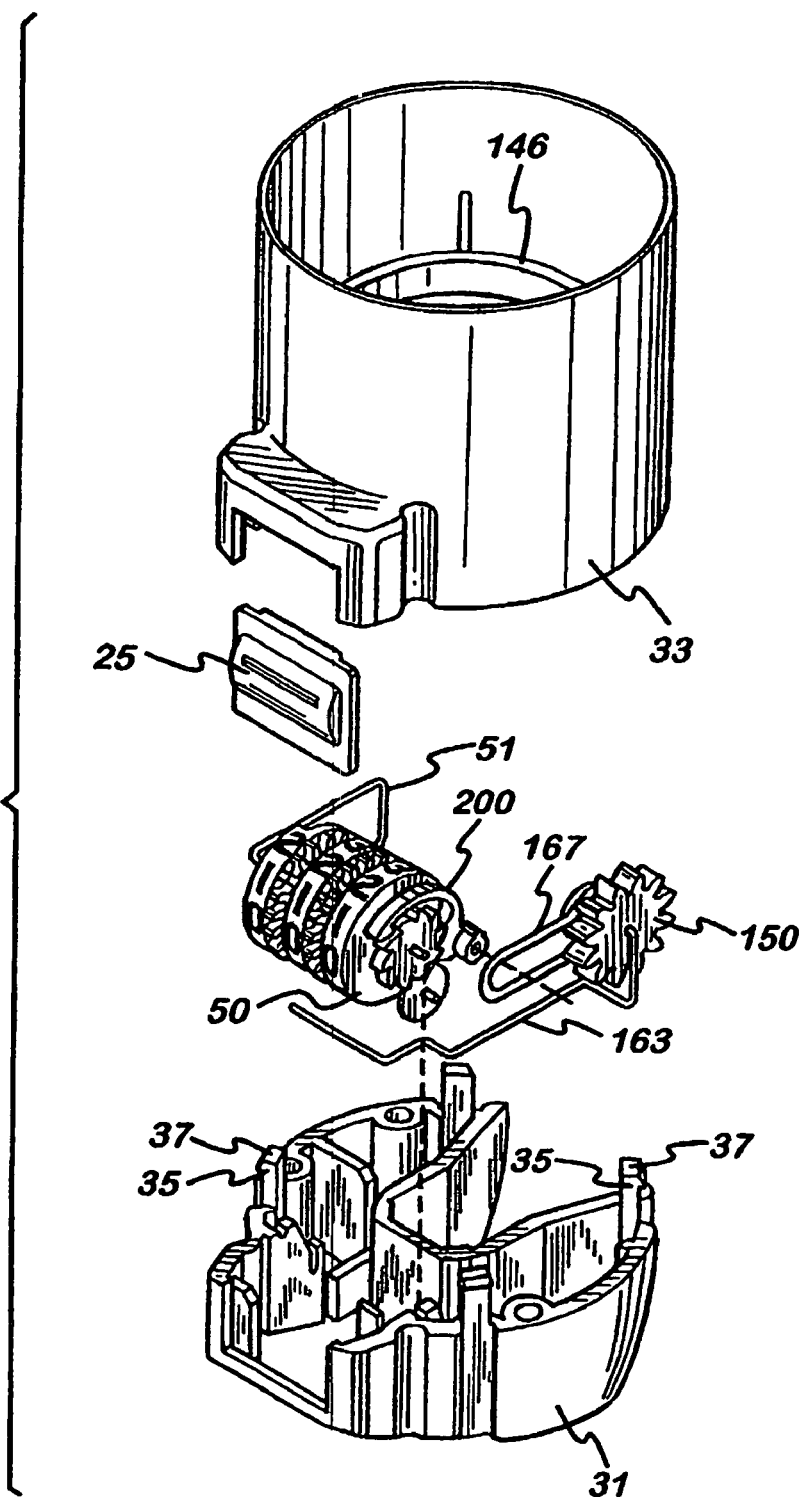
FIG. 3 is a further exploded perspective view of the dose counter module, but with a drums sub-assembly and drive wheel sub-assembly of the dose counter in assembled form.

Referring now to FIGS. 18 to 21, a preferred sleeve part 33 is shown. This sleeve part 33, like the one shown in FIGS. 1 to 3, is adapted to be attached to a cap part 31 (see FIG. 5) to form a casing for a dose counter module 19. It has four holes 131, 132, 133, 134 for receiving posts 35 on the cap part 31. Two of the holes 131, 132 are cylindrical for receiving cylindrical posts 35. The other two holes are generally cylindrical but with a flattened part (i.e. generally D shaped) for receiving correspondingly shaped posts 35 on the cap part 31.

The two non-cylindrical holes 133, 134 are relatively rotated so that the cap part 31 can only be fitted in one orientation even if the posts 35 are symmetrically arranged.

Differently shaped holes could be provided, and would need to be provided for differently shaped posts 35 such as those shown in FIG. 4 (only one post 35 is non-cylindrical) or FIG. 3 (the posts 35 have a square section, with hook clips 37 on the ends thereof).

Two posts 135 are also provided on the sleeve part 33 extending from the bottom 137 thereof. These posts 135 engage into holes 136 provided in the cap part 31 (see FIG. 5). The posts 135 on the sleeve part 33 are shorter than the posts 35 on the cap part 31.

The sleeve part 33 is generally cylindrical. However, in the bottom 137, there is moulded a base moulding having a generally U-shaped configuration to match the U-shaped configuration of the cap part 31 defined by the concave cut-out 41 (see, e.g., FIG. 4). This U-shaped base moulding further defines the position for the canister's valve stem 27 (see FIGS. 22 and 23) and the stand or stem block 13 (described above with reference to the prior art) to fit into. Further it defines part of the protrusion 23 described above (the protrusion 23 receives the window 25).

The base moulding extends from the bottom 137 of the sleeve part 33 up to a base wall 139. The outlet end of the canister 17 may, in use, rest against an upper side of this base wall 139 (or on supports provided thereon), as will be described with reference to FIGS. 22 and 23 below. The moulding, on its lower side, however, provides, in combination with the cap part 31, a cavity into which the indexing or counting mechanism, such as the drums sub-assembly 50, can be fitted. See FIGS. 22 and 23.

The cylindrical portion 140 of the sleeve part 33 can accept more than one style of canister 17, in this embodiment different styles of valve assembly. As an example, FIG. 22 shows a canister 17 which is fitted with a first type of valve assembly 250. FIG. 23 shows the canister 17 fitted with a second, different type of valve assembly 300 (i.e. the can is the same, but the valve assembly differs). As will be seen, the valves 250,300 have valve stem ends 29 (or ferrules) of different shape. In the first valve assembly 250, there is a small nose 49 adjacent the valve stem 27. The nose 49 of the second valve assembly 300, however, is much longer, axially. Moreover, the valve assemblies 250,300 protrude from the associated cans by a different distance D1,D2, i.e. the valve assemblies 250,300 have a different thickness. So, the valve stems 27 are spaced outboard from the can at different distances D1,D2.

As a result of these differences, the canisters 17 sit differently in the sleeve part 33. However, it is important that the tip of each valve stem 27 be positioned at a common, or substantially common, position relative to a reference surface of the dose counter module 19, e.g. the base wall 139. In other words, the spatial position of the tip of each valve stem 27 in the dose counter module 19, when assembled to the respective aerosol canister 17, must be the same, or substantially the same. Expressed another way, the valve stems 27 must be spaced at the same, or substantially same, distance from the reference surface of the dose counter module 19.

To this end, the upper side of the base wall 139 has two differently sized concentric supports or ledges 141, 142. The first ledge 141 comprises an annulus (see FIG. 20) extending upwards from the base wall 139. It has an appropriate height to support, in use, the first valve assembly 250, as shown by arrow 143 in FIG. 22. The second ledge 142 comprises a smaller annulus extending upwards from the base wall 139. It is concentric with the first ledge 141. However, it extends upwards to a lesser extent. It is adapted to support, in use, the second valve assembly 300, as marked by arrow 144 in FIG. 23.

The base wall 139 also comprises an aperture 145 in its centre, concentric with the two annuluses. The aperture 145 allows the valve stem 27 of the canister 17 to extend through the base wall 139 so that it can be inserted into the stand or stem block 333.

As shown in FIGS. 22 and 23, the ledges 141,142 respectively support the first and second valve assemblies 250,300 in the sleeve part 33 such that the valve stems 27 extend through the aperture 45 by the same distance, or substantially the same distance.

In this way, the rest positions in the actuator 3 of the aerosol canister units 15 incorporating the different valve assemblies 250,300 is the same, or substantially the same. This is because the spatial position of the valve stem tips in the respective dose counter module 19 is the same.

The sleeve part 33 also comprises a split ring collar 43, as previously described, for assisting in the connection of the sleeve part 33 to the canister 17 via the neck 47, which is annular. The wall 147 of the cylindrical portion 140 of the sleeve part 33 has an internal wall surface having a step or shoulder 146 for resting the collar 43 on. FIG. 3 shows this as a separately made ledge that is attached to the internal wall surface. The shoulder 146 assists in locating the collar 43 correctly for adhering or welding it to the sleeve part 33 for securing the canister 17 in the sleeve part 33 with the correct depth of insertion.

The top 138 of the wall 147 is chamfered also to assist in the insertion of the collar 43 and canister 17 into the sleeve part 33.

The above described components all can easily be fabricated and can be assembled using automated apparatus. Therefore they provide a more cost effective solution than the prior art.

Although the pMDI 1 described above with reference to the FIGURES of drawings is shown for oral inhalation, the mouthpiece 9 may be replaced with a nozzle for insertion into a patient's nostril, i.e. for intra-nasal use.

The therapeutic agent contained in the aerosol canister 17 may for the treatment of mild, moderate or severe acute or chronic symptoms or for prophylactic treatment. The therapeutic agent is preferably for treating respiratory diseases, e.g. asthma, chronic obstructive pulmonary disease (COPD), although may be for other therapeutic indications, e.g. treating rhinitis.

Appropriate therapeutic agents or medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti- inflammatories, e.g., beclomethasone (e.g. as the dipropionate ester), fluticasone (e.g. as the propionate ester), flunisolide, budesonide, rofleponide, mometasone (e.g. as the furoate ester), ciclesonide, triamcinolone (e.g. as the acetonide), 6α, 9α-difluoro-11β-hydroxy-16α-methyl-3-oxo-17α-propionyloxy-androsta-1,4-diene -17β-carbothioic acid S-(2-oxo-tetrahydro-furan-3-yl) ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl] amino]ethyl-2(3H) benzo-thiazolone; PDE4 inhibitors e.g. cilomilast or roflumilast; leukotriene antagonists e.g. montelukast, pranlukast and zafirlukast; [adenosine 2a agonists, e.g. 2R, 3R, 4S, 5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]; [α4 integrin inhibitors e.g. (2S)-3-[4-({[4-(aminocarbonyl)-1-piperidinyl]carbonyl}oxy)phenyl]-2-[((2S)-4-methyl-2-{[2-(2-ethylphenoxy)acetyl]amino}pentanoyl)amino]propanoic acid (e.g as free acid or potassium salt)], diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

Preferably, the medicament is formulated in a hydrofluoroalkane propellant, such as HFA-134a or HFA-227 or a combination thereof.

Preferably, the medicament is an anti-inflammatory steroid, such as a corticosteroid, for instance fluticasone, e.g. as the propionate ester, or a long acting beta agonist (LABA), such as salmeterol, e.g. as the xinafoate salt, or a combination thereof.

Preferred medicaments are salmeterol, salbutamol, albuterol, fluticasone and beclomethasone and salts, esters or solvates thereof, for instance fluticasone propionate, albuterol sulphate, salmeterol xinafoate and beclomethasone dipropionate.

The medicament may also be a glucocorticoid compound, which has anti-inflammatory properties. One suitable glucocorticoid compound has the chemical name: 6α, 9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α, 9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α, 9α-Difluoro-11β-hydroxy-16α-methyl-17β-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicaments may be delivered in combinations. As an example, there may be provided salbutamol (e.g. as the free base of the sulphate salt) or salmeterol (e.g. as the xinafoate salt) in combination with an anti-inflammatory steroid, such as beclomethasone (e.g. as an ester, preferably dipropionate) or fluticasone (e.g. as an ester, preferably propionate).

The actuation indicator of the present invention is not limited for use with an aerosol container, as in the example described with reference to the FIGURES of drawings, but may be used with other types of dispensing device. Moreover, the dispensing device need not necessarily be for dispensing medicament.

The present invention has been described above purely by way of example. Modifications, in detail, however, may be made within the scope of the invention, as defined in the claims appended hereto.

For the avoidance of doubt, the use of words herein such as "substantially", "generally", "about" and the like in relation to parameters or properties etc. is meant to encompass the absolute parameter or property as well as non-consequential deviations therefrom.

The invention claimed is:

1. An actuation indicator comprising a drums sub-assembly comprising a rotatable actuation indicator wheel, a rocking, ratchet pawl for rotating the indicator wheel in a set direction and a rocking mechanism for the pawl driven by a slipping clutch arrangement, wherein the slipping clutch arrangement comprises a slipping clutch spring engaged at one end to a pinion of a rack and pinion assembly and at a second end to the ratchet pawl.

2. The actuation indicator of claim 1, wherein the slipping clutch spring has a generally U-shaped configuration.

3. The actuation indicator of claim 2, wherein the open end of the spring engages a boss of the pinion and the closed end of the spring defines a track for slidingly engaging a boss provided on the pawl.

4. The actuation indicator of claim 1, wherein the ratchet pawl engages a ratchet wheel that is fixed to the indicator wheel.

5. The actuation indicator of claim 4, wherein a resilient, non-return leg engages a tooth of the ratchet wheel to prevent rotation of the ratchet wheel in a direction other than the set direction, and the non-return leg rides up and over the teeth to allow rotation in the set direction.

6. The actuation indicator of claim 1, wherein the drums sub-assembly further comprises at least one other indicator wheel, the indicator wheels being arranged to sequentially count down from a set figure to zero, and wherein the indicator wheels lock from further rotation in the set direction when they have counted down to zero, the slipping clutch spring then slipping on further attempts to rotate the mechanism.

* * * * *

UNITED STATES PATENT AND TRADEMARK OFFICE
CERTIFICATE OF CORRECTION

| | |
|---|---|
| PATENT NO. | : 7,500,444 B2 |
| APPLICATION NO. | : 10/518421 |
| DATED | : March 10, 2009 |
| INVENTOR(S) | : Bonney et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 983 days.

Signed and Sealed this
Nineteenth Day of August, 2014

Michelle K. Lee
*Deputy Director of the United States Patent and Trademark Office*